United States Patent
Schwartz et al.

(10) Patent No.: US 9,127,124 B2
(45) Date of Patent: Sep. 8, 2015

(54) LINEAR POLYESTERAMIDES FROM AMINOPHENOLIC ESTERS

(71) Applicants: TYRX, Inc., Monmouth Junction, NJ (US); Barbara Schwartz, East Windsor, NJ (US)

(72) Inventors: Arthur Schwartz, East Windsor, NJ (US); Satish Pulapura, Bridgewater, NJ (US); Sarita Nethula, Monmouth Junction, NJ (US); Archana Rajaram, Monmouth Junction, NJ (US); Arikha Moses, New York, NY (US)

(73) Assignee: TYRX, INC., Monmouth Junction, NJ (US)

( * ) Notice: Subject to any disclaimer, the term of this patent is extended or adjusted under 35 U.S.C. 154(b) by 0 days.

(21) Appl. No.: 14/491,102

(22) Filed: Sep. 19, 2014

(65) Prior Publication Data

US 2015/0004212 A1 Jan. 1, 2015

Related U.S. Application Data

(63) Continuation of application No. 13/766,136, filed on Feb. 13, 2013, now Pat. No. 8,952,106, which is a continuation of application No. 12/564,736, filed on Sep. 22, 2009, now Pat. No. 8,445,603.

(60) Provisional application No. 61/098,839, filed on Sep. 22, 2008.

(51) Int. Cl.

| | |
|---|---|
| *C08G 69/44* | (2006.01) |
| *A61K 9/00* | (2006.01) |
| *A61K 31/09* | (2006.01) |
| *A61K 31/4465* | (2006.01) |
| *A61K 31/496* | (2006.01) |
| *A61K 31/65* | (2006.01) |
| *A61K 31/7036* | (2006.01) |
| *A61L 29/06* | (2006.01) |
| *A61L 29/08* | (2006.01) |
| *A61L 31/06* | (2006.01) |
| *A61L 31/10* | (2006.01) |
| *C08L 77/12* | (2006.01) |
| *C08L 101/00* | (2006.01) |
| *C08G 69/00* | (2006.01) |
| *A61K 47/34* | (2006.01) |
| *A61L 29/14* | (2006.01) |
| *A61L 29/16* | (2006.01) |
| *A61L 31/14* | (2006.01) |
| *A61L 31/16* | (2006.01) |
| *A61M 25/00* | (2006.01) |

(52) U.S. Cl.
CPC .............. *C08G 69/44* (2013.01); *A61K 9/0024* (2013.01); *A61K 31/09* (2013.01); *A61K 31/4465* (2013.01); *A61K 31/496* (2013.01); *A61K 31/65* (2013.01); *A61K 31/7036* (2013.01); *A61K 47/34* (2013.01); *A61L 29/06* (2013.01); *A61L 29/085* (2013.01); *A61L 29/148* (2013.01); *A61L 29/16* (2013.01); *A61L 31/06* (2013.01); *A61L 31/10* (2013.01); *A61L 31/148* (2013.01); *A61L 31/16* (2013.01); *C08G 69/00* (2013.01); *C08L 77/12* (2013.01); *C08L 101/00* (2013.01); *A61L 2300/404* (2013.01); *A61L 2300/802* (2013.01); *A61L 2400/18* (2013.01); *A61L 2420/06* (2013.01); *A61M 2025/0057* (2013.01)

(58) Field of Classification Search
CPC . A61K 9/0024; A61K 31/09; A61K 31/4465; A61K 31/496; A61K 31/65; A61K 31/7036; A61K 47/34; A61L 29/06; A61L 29/085; A61L 29/148; A61L 29/16; A61L 2300/404; A61L 2300/802; A61L 2400/18; A61L 2420/06; A61M 2025/0057; C08G 69/00; C08G 69/44; C08L 77/12; C08L 101/00
See application file for complete search history.

(56) References Cited

U.S. PATENT DOCUMENTS

| | | |
|---|---|---|
| RE3,716 E | 11/1869 | Hall |
| RE3,779 E | 12/1869 | Jenkins |

(Continued)

FOREIGN PATENT DOCUMENTS

| | | |
|---|---|---|
| EP | 0051934 A1 | 5/1982 |
| EP | 0322788 A2 | 7/1989 |

(Continued)

OTHER PUBLICATIONS

JP Office Action for Application No. 2011-528070 dated Dec. 25, 2013.

(Continued)

*Primary Examiner* — Robert Jones, Jr.
(74) *Attorney, Agent, or Firm* — Sorell, Lenna & Schmidt, LLP

(57) ABSTRACT

The present invention is directed to linear, biodegradable polyesteramide (PEA) polymers synthesized with repeating units derived from aminophenol esters and diacids. These PEAs have a monomer repeat represented by

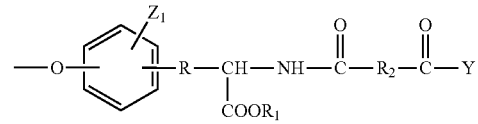

as well as a variety of uses to coat, form or comprise medical devices, combination medical devices and pharmaceutical compositions, including sustained release formulations.

21 Claims, 4 Drawing Sheets

(56) References Cited

U.S. PATENT DOCUMENTS

| | | | |
|---|---|---|---|
| 4,209,607 A | 6/1980 | Shalaby et al. |
| 4,272,625 A | 6/1981 | McIntyre et al. |
| 4,355,132 A | 10/1982 | East et al. |
| 4,387,210 A | 6/1983 | Katoh et al. |
| 4,428,932 A | 1/1984 | Overell |
| 4,555,566 A | 11/1985 | Arita et al. |
| 4,638,045 A | 1/1987 | Kohn et al. |
| 4,642,104 A | 2/1987 | Sakamoto et al. |
| 4,709,004 A | 11/1987 | Dai |
| 5,099,060 A | 3/1992 | Kohn et al. |
| 5,159,013 A | 10/1992 | Takida et al. |
| 5,185,424 A | 2/1993 | Casagrande et al. |
| 5,216,115 A | 6/1993 | Kohn et al. |
| 5,317,077 A | 5/1994 | Kohn et al. |
| 5,505,952 A | 4/1996 | Jiang et al. |
| 5,573,553 A | 11/1996 | McBride et al. |
| 5,587,507 A | 12/1996 | Kohn et al. |
| 5,658,995 A | 8/1997 | Kohn et al. |
| 5,670,602 A | 9/1997 | Kohn et al. |
| 6,048,521 A | 4/2000 | Kohn et al. |
| 6,120,491 A | 9/2000 | Kohn et al. |
| 6,284,862 B1 | 9/2001 | Kohn et al. |
| 6,319,492 B1 | 11/2001 | Kohn et al. |
| 6,475,477 B1 | 11/2002 | Kohn et al. |
| 6,503,538 B1 | 1/2003 | Chu et al. |
| 6,602,497 B1 | 8/2003 | Kohn et al. |
| 6,720,402 B2 | 4/2004 | Langer et al. |
| 6,852,308 B2 | 2/2005 | Kohn et al. |
| 7,056,493 B2 | 6/2006 | Kohn et al. |
| 7,202,325 B2 | 4/2007 | Pacetti et al. |
| 7,271,234 B2 | 9/2007 | Kohn et al. |
| 7,301,001 B2 | 11/2007 | Hossainy et al. |
| 7,361,726 B2 | 4/2008 | Pacetti et al. |
| 7,419,504 B2 | 9/2008 | Hossainy |
| 2002/0151668 A1 | 10/2002 | James et al. |
| 2003/0138488 A1 | 7/2003 | Kohn et al. |
| 2003/0216307 A1 | 11/2003 | Kohn et al. |
| 2004/0254334 A1 | 12/2004 | James et al. |
| 2005/0013793 A1 | 1/2005 | Beckman et al. |
| 2005/0165203 A1 | 7/2005 | Kohn et al. |
| 2005/0169968 A1 | 8/2005 | Elmaleh et al. |
| 2005/0260237 A1 | 11/2005 | Byun et al. |
| 2005/0265960 A1 | 12/2005 | Pacetti et al. |
| 2005/0288481 A1 | 12/2005 | DesNoyer et al. |
| 2006/0034888 A1 | 2/2006 | Pacetti et al. |
| 2006/0115449 A1 | 6/2006 | Pacetti |
| 2006/0173065 A1 | 8/2006 | Bezwada |
| 2006/0177480 A1 | 8/2006 | Sung et al. |
| 2006/0193891 A1 | 8/2006 | Richard |
| 2007/0009565 A1 | 1/2007 | Pacetti et al. |
| 2007/0020312 A1 | 1/2007 | DesNoyer et al. |
| 2007/0135355 A1 | 6/2007 | Bezwada |
| 2007/0198040 A1 | 8/2007 | Buevich et al. |
| 2007/0202147 A1 | 8/2007 | Kleiner et al. |
| 2007/0243256 A1 | 10/2007 | Kleiner et al. |
| 2007/0281031 A1 | 12/2007 | Yang |
| 2008/0014241 A1 | 1/2008 | DesNoyer et al. |
| 2008/0057127 A1 | 3/2008 | Bezwada |
| 2008/0095918 A1 | 4/2008 | Kleiner et al. |
| 2008/0112999 A1 | 5/2008 | Baluca |
| 2008/0132922 A1 | 6/2008 | Buevich et al. |
| 2008/0175882 A1 | 7/2008 | Trollsas et al. |
| 2008/0243049 A1 | 10/2008 | Hardy |
| 2009/0088548 A1 | 4/2009 | Moses et al. |
| 2010/0074940 A1 | 3/2010 | Schwartz et al. |
| 2010/0129417 A1 | 5/2010 | Moses et al. |
| 2010/0167992 A1 | 7/2010 | Schwartz et al. |

FOREIGN PATENT DOCUMENTS

| | | |
|---|---|---|
| EP | 0413375 A1 | 2/1991 |
| EP | 0856558 A1 | 8/1998 |
| EP | 0959091 A1 | 11/1999 |
| EP | 1229065 A1 | 8/2002 |
| JP | 57108129 A | 6/1982 |
| JP | 2000501139 A | 2/2000 |
| JP | 2008500387 A | 1/2008 |
| JP | 2010530921 A | 9/2010 |
| WO | 9719996 A1 | 6/1997 |
| WO | 9952962 A1 | 10/1999 |
| WO | 0149249 A2 | 7/2001 |
| WO | 0149311 A1 | 7/2001 |
| WO | 03091337 A1 | 11/2003 |
| WO | 2005068532 A1 | 7/2005 |
| WO | 2007028244 A1 | 3/2007 |
| WO | 2007098889 A1 | 9/2007 |
| WO | 2008112833 A1 | 9/2008 |
| WO | 2008157777 A1 | 12/2008 |

OTHER PUBLICATIONS

Brocchini et al., 1997, J. Amer. Chem. Soc. 119:4553-4554.
Carson et al., J Am Coll Cardiol, 40:418-423, 2002.
Clinical Orthopeadics &Rel. Res. 357: 219-228, 1998.
Crabtree et al., Semin Thorac Cardiovasc Surg., 16(1):53-61, 2004.
Department of Health and Human Services, 2007, vol. 72, No. 162.
Elias, et al. 1981 Makromol. Chem. 182:681-686.
Fakin et al., Infect Control Hosp Epidemiol 28(6):655-660, 2007.
Higashi et al., 1983, J. Polym. Sci.: Polym. Chem. Ed. 21:3241-3247.
Higashi et al., 1983, J. Polym. Sci.: Polynn. Chem. Ed. 21:3233-3239.
Higashi et al., 1986, J. Polym. Sci.: Polynn. Chem. Ed. 24:97-102.
Higashi et al., 1986, J. Polym. Sci: Polym. Chem. Ed. 24:589-594.
Hollenbeak et al. Infection Control and Hospital Epidemiology, 23(4): 177, 2002.
Hollenbeak et al., Chest, 118:397-402, 2000.
Hooper et al., 1998, J. Biomed. Mat. Res. 41:443-454.
International Search Report for Application No. PCT/US09/57860 dated Jan. 13, 2010.
Moore et al., 1990, Macromol. 23:65-70.
Ogata et al., 1981, Polym. J.,13:989-991.
Pulapura & Kohn, 1992, Biopolymers 32:41 1-417.
Pulapura et al., 1990, Biomaterials 11:666-678.
Rahmanian et al., Am J Cardiol, 100(11):1702-1708, 2007.
Tanaka et al. 1982, Polym. J. 14:643-648.
U.S. Appl. No. 60/375,846, filed Apr. 24, 2002.
Yasuda et al., 1983, J. Polym. Sci: Polym. Chem. Ed., 21:2609-2616.
Yokoe et al., Emerging Infectious Diseases, 10(11):1924-1930, 2004.
Australian Examination Report for Application No. 2009292949 dated Sep. 26, 2013.
Extended European Search Report for Application No. EP10783928 dated Jun. 17, 2013.
Canadian Office Action for Application No. 2,764,134 dated Nov. 22, 2012.
European Search Report for Application No. EP09815387 dated Jan. 14, 2013.
U.S. Appl. No. 12/791,586.

LINEAR POLYESTERAMIDES FROM AMINOPHENOLIC ESTERS

CROSS REFERENCE TO RELATED APPLICATIONS

The present application is a continuation of U.S. patent application Ser. No. 13/766,136, filed on Feb. 13, 2013, which is a continuation of U.S. patent application Ser. No. 12/564,736, filed on Sep. 22, 2009, which claims the benefit of the filing date of U.S. Provisional Application Ser. No. 61/098,839, filed Sep. 22, 2008, the disclosures of which are hereby incorporated herein by reference.

BACKGROUND OF THE INVENTION

Current progress in the medical device field is often focused on the combination product, i.e., devices that have a physical or mechanical function as well as pharmaceutical efficacy. One way to accomplish this is via the use of nonbiodegradable or biodegradable polymer systems as drug reservoirs for the combination products. Such polymer systems become the major contact point with tissue and, as such, should be biocompatible. Additionally, as combination products have become more complex, further desirable characteristics have been identified. For example, some polymer systems have been designed to be "biobeneficial," i.e., the polymers purportedly control protein adsorption and cell deposition (U.S. Pat. No. 7,186,789).

Polymers and polymer systems such as these act as the delivery vehicle for pharmaceutical agents to surrounding tissues and may serve other purposes in a combination product, including physical or mechanical functions. Polymeric delivery vehicles in combination products have taken the form of coatings for stents to deliver drugs (U.S. Pat. Nos. 7,056,591; 7,005,137; 6,953,560 and 6,776,796; and U.S. Pat. Appln. Pub. Nos. 2006/0115449 and 2005/0131201), coatings on surgical meshes to increase handling characteristics and/or for drug delivery (U.S. Pat. Appln. Pub. No. 2007/0198040), coatings for pacemaker pouches to stabilize the tissue pocket and deliver drugs (U.S. Pat. Appln. Pub. No. 2008/0132922), drug-eluting sutures (Ming et al., 2007), and drug-eluting breast implant covers (U.S. Ser. No. 12/058,060, filed Mar. 28, 2008).

As medical providers and patients require greater product performance, the demands placed upon the polymer as an active entity have increased. For example, some of the original stent coatings were polymeric films wrapped around the stent. These films delivered drug directly to the vessel wall by the force of stent expansion with the film being held in place by the stent itself (U.S. Pat. Nos. 5,634,946 and 5,674,287). Current research in the stent coating field focuses on optimizing polymer biocompatibility (WO 2007/056134, U.S. Pat. Nos. 5,317,077; 5,216,115; and 5,099,060), melt viscosity (U.S. Pat. Appln. Pub. No. 2008/0187567), protein adsorption characteristics (U.S. Pat. Appln. Pub. No. 2006/0115449), hydrophilicity, or physicomechanical characteristics (U.S. Pat. Appln. Pub. No. 2005/0131201).

While many polymer classes are known and a variety of those are being used in combination products, synthetic polymers containing the amino acid tyrosine confer many advantages and opportunities to optimize polymer properties. These advantages are partially derived from tyrosine's inherent biocompatibility, lack of toxicity, aromatic nature, and three potential polymerization sites, i.e. the phenolic hydroxyl group, the amino group, and the carboxylic acid group.

One of tyrosine's original uses in a synthetic polymer arose from Kohn's and Langer's work with tyrosine dipeptides wherein an amino-protected tyrosine was dimerized with a tyrosine ester to form a monomeric, diphenolic compound. That di-tyrosine diphenol was copolymerized with dicyanate to produce tyrosine-based polyiminocarbonates to create new immunomodulatory agents (U.S. Pat. No. 4,863,735). Subsequently, Kohn invented several polymeric classes of tyrosine-based polymers in which a tyrosine ester was dimerized with a des-aminotyrosine (i.e., tyrosine lacking its amino group) to form a "tyrosine-derived diphenol." Those diphenols were condensed with reagents containing two active sites to form several different polymeric classes, including "polyarylates" (polyesters) and polycarbonates (e.g., U.S. Pat. Nos. 7,271,234; RE 37,795E; RE 37,160E; 5,216,115; 5,099,060), polyiminocarbonates (e.g., U.S. Pat. No. 4,980,449), polyethers, polythiocarbonates, polyphosphonates (e.g., U.S. Pat. No. 5,912,225) and others. A later developed group of tyrosine-derived diphenolic polymers, in which the tyrosine side chain ester is converted to a free acid after polymerization has been shown to be an extremely versatile, biocompatible family of materials (U.S. Pat. No. 6,120,491).

Tyrosine-derived diphenolic polyarylates are finding application in antimicrobial-eluting combination devices such as hernia repair meshes and pacemaker covers. They have also been used for combination drug-device products such as drug-eluting stent coatings, breast implant covers, and other applications. Tyrosine-derived diphenolic polycarbonates are being used as fully resorbable cardiovascular stents (Kohn et al., 2005).

Other tyrosine-derived diphenolic polymers have been described by Pacetti et al. (U.S. 2006/0115449). These polymers include tyrosine-derived diphenolic polycarbonates and polyiminocarbonates for use as drug-eluting stent coatings. Pacetti noted that his "tyrosine dipeptide-based bioabsorbable polymers" have mechanical strength advantages because the diphenolic moiety increases rigidity and provides higher glass transition temperatures (Tg). Kohn et al. and Baluca (U.S. Pat. Appln. Pub. Nos. 2008/0187567 and 2008/0112999, respectively) disclosed N-substituted monomers and polymers containing tyrosine-derived diphenols and indicated that protecting the nitrogen appeared to confer a lower glass transition temperature compared to the unprotected species, apparently lowering it enough to confer processability to the materials. Moses et al. have disclosed tyrosine-derived diphenolic monomers and polymers with side chain amides instead of esters (WO 2007/056134).

When copolymerized with the appropriate components, tyrosine provides assets for resorbable combination medical device products such as lack of toxicity, biocompatibility and rigidity. For example, Kohn's tyrosine-derived diphenolic polycarbonates (U.S. Pat. No. 5,198,507) and polyarylates (U.S. Pat. No. 5,216,115) lend rigidity to a device because of their relatively high glass transition temperatures compared to poly-lactic and glycolic acid-based systems. While the glass transition temperature in these polymer families can be moderated by increasing the number of carbons in the backbone or side chain of the polymer (Brocchini et al., 1997), the resorption times for most of these polyarylates are in excess of one year and in excess of 5-10 years for the corresponding polycarbonates (Tangpasuthadol et al., 2000a; Tangpasuthadol et al., 2000b).

Because these polymers do not generally meet the resorption time requirements for the bulk of the resorbable medical products, which require resorption times that vary anywhere from several weeks to several months (e.g., resorbable PGA or PLGA sutures (Ethicon)) to three to six months (cardiovascular stent coatings and/or drug delivery systems (Conor, Biosensors), these polymers are not adequate for many medical needs. Moreover, long resorption times make regulatory hurdles prohibitively expensive because biocompatibility at the implant site of choice may need to be shown through full resorption. For example, any product with a polymer coating that takes 2 years to resorb will require at least a 2-year preclinical program followed by a 2-3 year clinical program in advancing towards regulatory approval.

Thus, the polymer resorption time, along with physicomechanical properties, biocompatibility and drug elution times will contribute to the success of a significant number of combination products. While Kohn reduced the resorption time of the tyrosine-derived diphenolic polyarylates and polycarbonates to a limited extent via the selective introduction of free acid side chains into the diphenolic monomer structures (U.S. Pat. No. 6,120,491), the introduction of those side chains significantly increased the complexity and cost of the synthesis of these materials as well as the glass transition temperature (in some cases, out of the range of polymer processability (U.S. Pat. Appln. Pub. No. 2008/0187567). Furthermore, while the addition of free acid side chains decreased the resorption time for those polymeric fragments containing the free acid side chain, the degradation process still left long polymeric fragments containing ester side chains with resorption times equivalent to those of the original polymer that did not contain the free acid (U.S. Pat. No. 6,120,491).

Therefore, the need remains for a biodegradable, biocompatible family of polymers with resorption times of less than one year, and preferably for a subset with resorption times of less than 6 months that have an accompanying drug elution potential as well as glass transition temperatures in the useful range of 20-85° C. The present invention addresses these shortcomings in the art and more by providing linear polyesteramides formed from aminophenol esters, e.g., tyrosine esters and the like, and diacids in the manner described herein. Moreover, while the polymers of the instant invention can incorporate both free acid side chains and esterified side chains, these polymers do not require the presence of free acid side chains to provide fast resorption times, making them cheaper and easier to synthesize than the polymers disclosed in U.S. Pat. No. 6,120,491.

SUMMARY OF THE INVENTION

The present invention is directed to polymers that are biodegradable polyesteramide (PEA) polymers and, with appropriate selection of the various R groups, a substantial number of the polymers are capable of resorption under physiological conditions in medically relevant time periods. Moreover, these properties are achieved via inexpensive and simple synthetic routes, while providing polymers with the robust mechanical and physical characteristics as well as lack of toxicity associated with the presence of tyrosine and related aromatics.

Accordingly, the synthetic PEA polymers of the invention comprise aminophenol-diacid repeating units represented by the formula

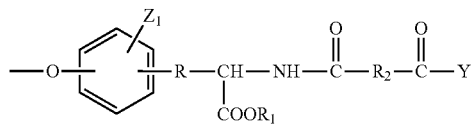

wherein

R is —(CR$_3$R$_4$)$_a$— or —CR$_3$=CR$_4$—;

R$_1$ is hydrogen; saturated or unsaturated alkyl, aryl, alkylaryl or alkyl ether having from 1 to 20 carbon atoms; or —(R$_5$)$_q$O((CR$_3$R$_4$)$_r$O)$_s$—R$_6$;

each R$_2$ is independently a divalent, linear or branched, substituted or unsubstituted alkylene, alkenylene, alkynylene, arylene, alkylarylene, alkyl ether or aryl ether moiety having from 1 to 30 carbon atoms; —R$_5$)$_q$O((CR$_3$R$_4$)$_r$O)$_s$(R$_5$)$_q$—; or —(R$_5$)$_q$CO$_2$((CR$_3$R$_4$)$_r$O)$_s$CO(R$_5$)$_q$—;

R$_3$ and R$_4$ are each independently, hydrogen or linear or branched, substituted or unsubstituted alkyl having from 1 to 10 carbon atoms, R$_5$ is independently linear or branched, lower alkylene or lower alkenylene;

R$_6$ is independently linear or branched, substituted or unsubstituted, saturated or unsaturated lower alkyl;

the aromatic ring has from zero to four Z$_1$ substituents, each of which is independently selected from the group consisting of halide, lower alkyl, alkoxy, nitro, alkyl ether, a protected hydroxyl group, a protected amino group and a protected carboxylic acid group;

Y is

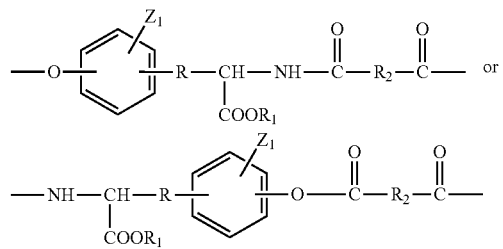

a is 0 to 10;

each q is independently 1 to 4;

each r is independently 1 to 4; and each s is independently 1 to 5000.

In particular embodiments, the polymers of the invention comprise from at least about 0.01% to 100% of the repeating unit and thus include copolymers and homopolymers.

Another aspect of the invention is directed to polymers of the invention blended with one or more second polymers. The second polymers are also biocompatible but can be biodegradable, resorbable or stable as needed for the particular use. A nonlimiting list of particularly useful second polymers, especially for fully resorbable products, include polyethylene glycol (PEG), poly(D,L-lactide) (PLA), polyglycolic acid [polyglycolide (PGA)], poly(D,L-lactide-co-glycolide) (PLGA) and diphenol-derived or tyrosine-derived diphenol polyarylates and polyiminocarbonates and the like. The polymers blends of the invention can further include one or more drugs and thus include pharmaceutical compositions.

In yet another aspect of the invention, the polymers and/or blends of the invention can be formulated into pharmaceutical compositions comprising one or more drugs, and optionally, one or more pharmaceutically-acceptable carriers to provide formulations with varying drug release profiles and characteristics. Such drugs include, but are not limited to, antimicrobial agents, anesthetics, anti-inflammatory agents, anti-scarring agents, growth factors, anti-neoplastic agents and anti-fibrotic agents. The pharmaceutical compositions include a range of physical formulations, including microspheres, microparticles, rods, pastes, films, creams, tablets or the like.

In a further aspect, this invention provides medical devices comprising or formed from one or more of the PEA polymers or polymer blends of the invention, with or without one or more drugs. The invention further includes medical devices that are coated with one or more of the PEA polymers or polymer blends of the invention, again with or without one or more drugs. Such devices include but are not limited to, implantable or insertable devices such as stents; surgical meshes; coverings, pouches, pockets, bags and the like that can be used in conjunction with another device (e.g., pacemakers, difibrillators, neurostimulators, implantable pumps, breast implants); wound closure adjuncts; flat sheets or films for use alone or in conjunction with another medicil device; and any type of catheter. Coatings as used in the instant invention, when present, can be disposed on any surface of the device as a partial or full coating and can be single- or multi-layered. The coatings can include blends with other polymers of the invention or other biocompatible polymers, with and without one or more drugs as appropriate to the use or need.

In a still further aspect, the instant invention provides methods of preventing, treating or ameliorating a disorder or condition in a patient by implanting a medical device of the invention (with or without one or more drugs) in a patient or administering a therapeutically-effective amount of a pharmaceutical composition of the invention. Implantable or injectable compositions and medical devices of the invention can be used to treat or ameliorate a cardiovascular disorder, a neurological disorder, a hernia or hernia-related disorder, an ophthalmic condition, or to effectuate an anatomical repair, reconstruction, replacement or augmentation of a body part, limb, tissue or organ of a patient, or to stabilize an implantable device, including pulse generators, defibrillators, implantable pumps, breast implants and the like. Hence, the methods of the invention can prevent or ameliorate, for example, the morbidities associated with implantation of comparable untreated medical devices, including scarring, pain and infection.

In a yet still further aspect, the present invention is directed to a method of synthesizing a strictly alternating PEA polymer by reacting about two equivalents of an aminophenol and about one equivalent of a first diacid with a coupling agent for a time and under conditions to preferentially form amide bonds and produce an aminophenol-diamide-aminophenol trimer; recovering the trimer and further reacting it with a about one equivalent of a second diacid in the presence of a second coupling agent for a time and under conditions to form said PEA polymer and recovering the polymer. This synthesis method allows one to easily vary the diacids and aminophenols in the PEA polymer in a predictable structural manner.

DETAILED DESCRIPTION OF THE INVENTION

Definitions and Abbreviations

Figure 1:
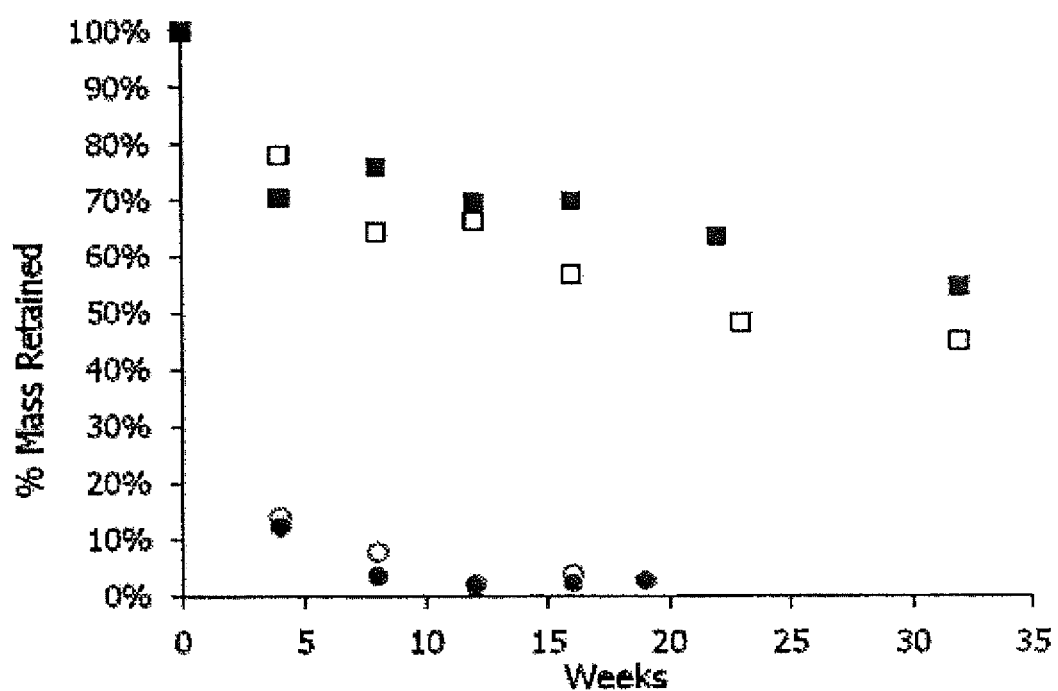
FIG. 1 graphically illustrates mass retained under physiological degradation conditions for random and alternating polymers on polymer-coated meshes: (□) TE glutarate alternating; (■) TE glutarate random; (●) TE diglycolate alternating; (○) TE diglycolate random.

The compounds herein described may have asymmetric centers. All chiral, diastereomeric, and racemic forms are included in the present invention. Geometric isomers of olefins and the like can also be present in the compounds described herein, and all such stable isomers are contemplated in the present invention.

By "stable compound" or "stable structure" is meant herein a compound or molecule that is sufficiently robust to survive isolation to a useful degree of purity from a reaction mixture, and for formulation or use.

As used herein, unless otherwise clear from the context, "alkyl" means both branched- and straight-chain, saturated aliphatic hydrocarbon groups having the specified number of carbon atoms. Straight and linear are used interchangeably. As used herein "lower alkyl" means an alkyl group having 1 to 6 carbon atoms. When substituted, the substituents can include halide, alkyl, alkoxy, hydroxy, amino, cyano, nitro, trifluoromethyl, trifluoroethyl, additional substituents as described herein, and the like compatible with the synthesis of the molecules of the invention.

As used herein, "alkenyl" means hydrocarbon chains of either a straight or branched configuration and which have one or more unsaturated carbon-carbon double bonds, such as ethenyl, propenyl, and the like. "Lower alkenyl" is an alkenyl group having 2 to 6 carbon atoms. As used herein, "alkynyl" means hydrocarbon chains of either a straight or branched configuration and which have one or more carbon-carbon triple bonds, such as ethynyl, propynyl and the like. "Lower alkynyl" is an alkynyl group having 2 to 6 carbon atoms. When the number of carbon atoms is not specified, then alkyl, alkenyl and alkynyl means having from 1-20 carbon atoms. Alkylene, alkenylene, and alkynylene groups are alkyl, alkenyl, and alkynyl groups, respectively, which are divalent. When substituted, the substituents of the alkylene, alkenylene, and alkynylene groups can include halide, lower alkyl, alkoxy, hydroxy, amino, cyano, nitro, trifluoromethyl, trifluoroethyl, additional substituents as described herein, and the like compatible with the properties and synthesis of the molecules of the invention.

As used herein, "saturated or unsaturated alkyl" refers to any of an alkyl group an alkenyl group or an alkynyl group, having any degree of saturation, i.e., completely saturated (as in alkyl), one or more double bonds (as in alkenyl) or one or more triple bonds (as in alkynyl).

Examples of alkyl groups include but are not limited to, methyl, ethyl, n-propyl, isopropyl, n-butyl, isobutyl, t-butyl, pentyl, hexyl, cyclohexyl, n-heptyl, n-octyl, isooctyl, nonyl, decyl, and the like; alkylene and alkenylene groups include but are not limited to, methylene, ethylene, propylenes, propenylene, butylenes, butadiene, pentene, n-hexene, isohexene, n-heptene, n-octene, isooctene, nonene, decene, and the like. Those of ordinary skill in the art are familiar with numerous linear and branched hydrocarbon groups. Alkynyl groups include ethynyl and propynyl groups, and alkynylene groups include —C≡C—, —C≡C—CH$_2$—, —CH$_2$—C≡C—CH$_2$—, —CH$_2$—C≡C—CH$_2$CH$_2$—, etc.

As used herein, "aryl" means any stable 6- to 14-membered monocyclic, bicyclic or tricyclic ring, containing at least one aromatic carbon ring, for example, phenyl, naphthyl, indanyl, tetrahydronaphthyl (tetralinyl) and the like. When substituted, the substituents can include halide, alkyl, alkoxy, hydroxy, amino, cyano, nitro, trifluoromethyl, trifluoroethyl, or additional substituents as described herein, and the like compatible with the properties and synthesis of the molecules of the invention. Arylene refers to a divalent aryl group.

As used herein, "alkylaryl" refers to moiety in which an aryl group is attached to an alkyl group, which in turn is the attachment point of the substituent to the molecule. For example, a benzyl ester represents an alkylaryl moiety in which the methylene attached to a phenyl ring is bonded to the oxygen of the ester in the formula COOR, where R is the benzyl ester. The aryl group of this moiety can optionally be substituted in accordance with the definitions herein. In analogy to alkylene, arylene, etc., an alkylarylene is a divalent alkylaryl group.

The term "substituted" as used herein means that one or more hydrogens on the designated atom are replaced with a selection from the indicated groups, provided that the designated atom's normal valency is not exceeded, and that the substitution results in a stable compound. Unless otherwise clear from the context, if no substituent is indicated, the valency is filled with a hydrogen.

The terms "radical," "group," "functional group," and "substituent" can be used interchangeably in some contexts and can be used together to further describe a chemical structure. For example, the term "functional group" can refer to a chemical "group" or "radical," which is a chemical structure variable that can be in-chain, pendant and/or terminal to the chemical structure. A functional group may be substituted.

A "halide" or a "halo" group is a halogen atom, and includes fluoro, chloro, bromo and iodo groups. The term "alkoxy" refers to an alkyl group having at least one oxygen substituent represented by R—O—.

Abbreviations used herein for naming polymers and the subunits thereof include Bn or Bz, benzyl; D, des-aminotyrosine; dg or dlg, diglycolate; E or Et, ethyl; glu, glutarate; M or Me, methyl; P, 4-hydroxyphenylglycine; PEG, polyethylene glycol; PPG, polypropylene oxide; succ, succinate; T, tyrosine; and TE, tyrosine ethyl ester.

Polymer Description:

The present invention is directed to biodegradable PEA polymers. These synthetic polymers comprise one or more repeating units represented by the formula

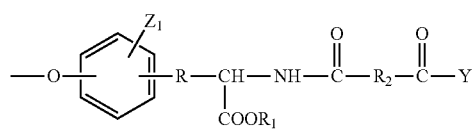

wherein
R is —(CR$_3$R$_4$)$_a$— or —CR$_3$=CR$_4$—;
R$_1$ is hydrogen; saturated or unsaturated alkyl, aryl, alkylaryl or alkyl ether having from 1 to 20 carbon atoms; or —(R$_5$)$_q$O((CR$_3$R$_4$)$_r$O)$_s$—R$_6$;
each R$_2$ is independently a divalent, linear or branched, substituted or unsubstituted alkylene, alkenylene, alkynylene, arylene, alkylarylene, alkyl ether or aryl ether moiety having from 1 to 30 carbon atoms; —(R$_5$)$_q$O((CR$_3$R$_4$)$_r$O)$_s$(R$_5$)$_q$—; or —(R$_5$)$_q$CO$_2$((CR$_3$R$_4$)$_r$O)$_s$CO(R$_5$)$_q$—;
R$_3$ and R$_4$ are independently, hydrogen or linear or branched, substituted or unsubstituted alkyl having from 1 to 10 carbon atoms,
R$_5$ is independently linear or branched, lower alkylene or lower alkenylene;
R$_6$ is independently linear or branched, substituted or unsubstituted, saturated or unsaturated lower alkyl;
the aromatic ring has from zero to four Z$_1$ substituents, each of which is independently selected from the group consisting of halide, lower alkyl, alkoxy, nitro, alkyl ether, a protected hydroxyl group, a protected amino group and a protected carboxylic acid group;
Y is

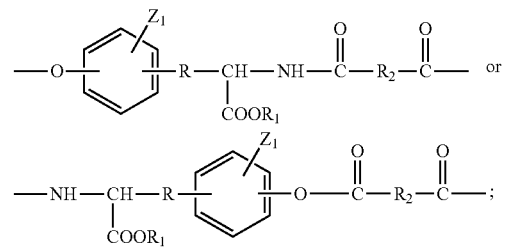

a is 0 to 10;
each q is independently 1 to 4;
each r is independently 1 to 4; and
each s is independently 1 to 5000.

These polymers are biodegradable PEA polymers having aminophenol units and diacid units which can be generally represented by the formula p(-AP-X—)$_n$, where n is the actual number or the weight average number of repeat units in the polymer. The aminophenols (AP) have the structure shown in Formula I (I)

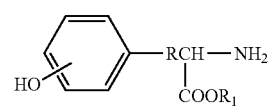

and the diacids (X) have the structure shown in Formula II (II)

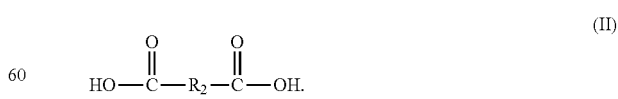

When these monomeric units are polymerized under condensation conditions (or other precursors depending on the synthesis route), the resultant polymers have backbones with both ester and amide bonds, and side chains with ester or free acids (depending on the choice of R$_1$). While the repeat motif of the polymer has the structure AP-X, this simple representation of the polymer does not reflect the various coupling permutations of the aminophenol and the diacid, i.e., whether the coupling between the aminophenol and the diacid occurs via reaction of the AP's amine functional group with one of the acid groups to produce an amide linkage or via reaction of the AP's hydroxyl functional group with one of the acid groups to produce an ester linkage. Hence, the AP-X repeat unit can be represented by the either structure below ("repeat a" or "repeat b", respectively).

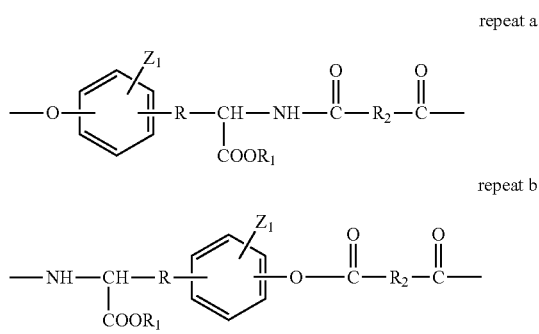

However, this simple structural representation (-AP-X—) does not show the relative relationship of these units to one another since these units can be further joined together by either an amide or ester bond. Hence, the actual structures of the polymers of the present invention which contain the aminophenol and diacid moieties described herein, depend on the choice of synthetic route, the choice of coupling agents and the selective reactivity in forming amide or ester bonds.

Accordingly, the polymers of the invention are random copolymers of repeats a and b or strictly alternating copolymers of repeat a, repeat b or both repeats a and b, with the particular polymer structure determined by the method of synthesis as described herein.

For purposes of nomenclature, random copolymers of repeats a and b, are denominated by the simple formula p(-AP-X—), AP-X or as random ab polymers, such names being used interchangeably. Names for this polymer class are based on these representations so that random ab polymers are named for the aminophenol moiety followed by the diacid moiety, regardless of the starting materials. For example, a polymer made by random copolymerization of tyrosine ethyl ester (TE) as the aminophenol moiety with succinic acid as the diacid moiety is referred to as p(TE succinate) or TE succinate. If the diacid moiety were changed to glutaric acid, this random copolymer would be p(TE glutarate) or TE glutarate. For additional clarity or emphasis, the word random may be appended to the polymer name, e.g., TE succinate random or p(TE succinate) random. If the polymer is designated without anything after the name, then the polymer is a random copolymer.

There are two strictly alternating copolymers classes that can be obtained from these monomeric units: (1) a linear string of a single repeat, either "repeat a," thus in format $(a)_n$ or "repeat b," thus in format $(b)_n$, which are equivalent formats; or (2) a linear string of alternating "repeat a" and "repeat b," thus in form $(ab)_n$ or $(ba)_n$, which are equivalent representations for these polymers. In all cases, n is the number of repeat units. For polymers, n is usually calculated from the average molecular weight of the polymer divided by the molecular weight of the repeat unit.

For purposes of nomenclature, strictly alternating polymers of the $(a)_n$ form are referred to as p(—O-AP-X—) or as alternating "a" polymers. Alternating "a" polymers occur when the reaction conditions are such that the free amine of the aminophenol reacts first with the diacid (or other appropriate reagent) as controlled by the reaction condition, forming an amide linkage and leaving the hydroxyl free for further reaction. For example, a polymer made by copolymerization of tyrosine ethyl ester (TE) as the aminophenol moiety with succinic anhydride (to provide the diacid moiety) leads to an alternating "a" polymer and is referred to herein as p(O-TE succinate) or O-TE succinate.

For purposes of nomenclature, polymers of the $(ab)_n$ form are referred to as $p(-AP-X_1-AP-X_2—)$, $p(AP-X_1AP—X_2)$ or as $AP-X_1-AP X_2$, when having a and b repeats with different diacids or as "p(-AP-X—) alternating" or as AP-X alternating, when the a and b repeats have the same diacid.

Polymers with two different diacids can be made, for example, by reacting two equivalents of an aminophenol with one equivalent of a first diacid under conditions that favor amide bond formation and isolating the reaction product, a compound having the structure $AP-X_1-AP$, which is also referred to herein as a trimer because it consists of two aminophenol units and one diacid unit. This trimer is reacted with a second diacid under polymerization conditions to produce the polymer $p(AP-X_1AP-X_2—)$ if the second diacid is different from the first diacid, or to produce the polymer p(-AP-X—) alternating if the second diacid is the same as the first diacid. As an illustration, an initial trimer made from TE and succinic acid is denominated as TE-succinate-TE. Reaction of TE-succinate-TE with glutaric acid produces the polymer p(TE-succinate-TE glutarate), whereas reaction with succinic acid produces the polymer p(TE succinate) alternating. The polymers of the invention also include polymers made with mixed aminophenol repeats, mixed diacid repeats and mixed trimer repeats, or any combination of such mixtures. For these complex polymers, the mixed moiety is designated by placing a colon between the names of the two moieties and indicating the percentage of one of the moieties. For example, p(TE:10TBz succinate) random is a polymer made by using a mixture of 90% tyrosine ethyl ester and 10% tyrosine benzyl ester with an equimolar amount of the diacid succinic acid under random synthesis conditions. An example of a strictly alternating $(ab)_n$ polymer with a mixed second diacid is p(TE-diglycolate-TE 10PEG-bis-succinate:adipate). This polymer is made by preparing the TE-diglycolate-TE trimer and copolymerizing it with a mixture of 10% PEG-bis-succinic acid and 90% adipic acid. An example of a strictly alternating $(ab)_n$ polymer with mixed trimers is p(TE-succinate-TE:35TE-glutarate-TE succinate). This polymer is made by conducting a separate synthesis for each trimer, mixing the isolated trimers in the indicated ratio (65 mol % TE-succinate-TE/35 mole % TE-glutarate-TE) and copolymerizing with an equimolar amount of succinic acid. With such complexity, it is often simpler to list the various components and relative amounts in a table, especially for strictly alternating $(ab)_n$ polymers. Table 1 provides examples of some strictly alternating $(ab)_n$ polymers. In Table 1, $T_g$ is the glass transition temperature of the polymer after synthesis. Mol. Wt. is the weight average molecular weight $(M_w)$ of the polymer after synthesis as determined by gel permeation chromatography.

Examples of polymers of the invention include, but are not limited to, those shown in Table 1 as well as polymers (1) wherein the aminophenol unit in the polymer is provided by a tyrosine ester such as tyrosine methyl ester, tyrosine ethyl ester, tyrosine benzyl ester, free tyrosine, or a methyl, ethyl, propyl or benzyl ester of 4-hydroxyphenylglycine as well as 4-hydroxyphenylglycine, and (2) wherein the diacid unit is succinic acid, glutaric acid, adipic acid, diglycolic acid, dioxaoctanoic acid, a PEG acid or a PEG bis-diacid (e.g., PEG-bis-succinate or PEG-bis-glutarate). For polymers with mixed aminophenol repeats, the polymer contains from about 5 to about 40% or from about 10 to about 30% of a first aminophenol repeat with the remainder being the second aminophenol repeat. For polymers with mixed diacid repeats, the polymer contains from about 10 to about 45% or from about 20 to about 40% of a first diacid repeat with the remainder being the second diacid repeat. For polymers with mixed trimer repeats, the polymer contains from about 5 to about 40% or from about 10 to about 30% of a first trimer with the remainder being the second trimer. Polymers made from any and all of the foregoing possible permutations are contemplated by the present invention. Additional examples of specific polymers of the invention include p(TE succinate), p(TE succinate) alternating, p(TE glutarate), p(TE glutarate) alternating, p(TE diglycolate), p(TE diglycolate) alternating, p(TE:15T glutarate), Tg 78, Mol. wt. 74 kDa; and p(TE:15TBz glutarate). This last polymer is an example of an intermediate polymer used in preparation of p(TE:15T glutarate); i.e., the benzyl ester of TBz is converted to the free carboxylic acid by removing the benzyl group using known methods, for example by hydrogenation.

Other polymers of the invention include those in which a strictly alternating polymer has been synthesized with a trimer selected from the group consisting of TE-succinate-TE, TE-glutarate-TE, TE-adipate-TE, TE-diglycolate-TE, and TE-X-TE monomers wherein X is comprised of a PEG unit with or without other species, such as a PEG bifunctionalized via condensation with two equivalents of a diacid such as succinic acid, glutaric acid, adipic acid, diglycolic acid, or others. Any of these trimers can be copolymerized with a diacid repeat selected from the group of succinic acid, glutaric acid, adipic acid, diglycolic acid, dioxaoctandioic acid, a PEG acid and a PEG bis-diacid (e.g., PEG-bis-succinate and PEG-bis-glutarate), or any mixture of these diacids or other diacids.

The glass transition temperatures for some of these polymers are provided in the Examples. Additionally, the $T_g$ for p(TE succinate) is 84° C. and the $T_g$ for p(TE:15T glutarate) is 78° C.

TABLE 1

| First Trimer AP-$X_1$-AP | % 1st | Second Trimer AP-$X_1$-AP | % 2d | First $X_2$ diacid | % 1st | Second $X_2$ diacid | % 2d | Tg (° C.) | Mol. Wt. (kDa) |
|---|---|---|---|---|---|---|---|---|---|
| TE-diglycolate-TE | 100 | | | PEG600 Acid | 25 | Glutaric acid | 75 | 25 | 111 |
| TE-diglycolate-TE | 100 | | | PEG400-bis-succinate | 25 | Glutaric acid | 75 | 29 | 130 |
| TE-succinate-TE | 65 | TE-(PEG400-bis-succinate)-TE | 35 | Succinic acid | 100 | | | 32 | 120 |
| TE-glutarate-TE | 100 | | | PEG400-bis-succinate | 35 | Succinic acid | 65 | 28 | 190 |
| TE-glutarate-TE | 100 | | | PEG400-bis-succinate | 35 | Glutaric acid | 65 | 26 | 199 |
| TE-glutarate-TE | 100 | | | Glutaric acid | 100 | | | 70 | 74 |
| TE-diglycolate-TE | 100 | | | Glutaric acid | 100 | | | 61 | |
| TE-diglycolate-TE | 100 | | | PEG600 Acid | 25 | Glutaric acid | 75 | 25 | |
| TE-diglycolate-TE | 100 | | | PEG600 Acid | 25 | Glutaric acid | 75 | 24 | |
| TE-diglycolate-TE | 100 | | | PEG400-bis-succinate | 25 | Succinic acid | 75 | 31 | |
| TE-diglycolate-TE | 100 | | | PEG400-bis-succinate | 25 | Glutaric acid | 75 | 29 | |
| TE-diglycolate-TE | 100 | | | PEG400-bis-succinate | 25 | Adipic acid | 75 | 25 | |
| TE-succinate-TE | 100 | | | Glutaric acid | 100 | | | | |
| TE-glutarate-TE | 100 | | | Succinic acid | 100 | | | | |
| TE-diglycolate-TE | 100 | | | Succinic acid | 100 | | | 72 | |

The polymers of the invention are biocompatible and biodegradable. A biocompatible polymer is a polymer which is compatible with living tissue or a living system and is acceptable for use in or by animals or humans. Thus, a biocompatible polymer does not cause physiological harm to any significant or unacceptable degree. For example, biocompatibility can be assessed by showing that a biocompatible polymer does not cause any or any significant amount of inflammation or immunological reaction or is not toxic or injurious to the living tissue or system. Hence, a biocompatible polymer can be ingested, implanted, inserted, injected, placed on or otherwise used in a living subject or tissue without untoward effects.

As used herein, a "biodegradable polymer" is a polymer that has hydrolytically or oxidatively labile bonds or that is susceptible to enzymatic action or other in vivo breakdown process, or any combination thereof, under physiological conditions. which action leads to the degradation and/or breakdown, whether partial or complete, of the polymer. It should be understood that polymers which are biodegradable have variable resorption times, which can depend, for example, on the nature and size of the breakdown products as well as other factors.

As used herein a "resorbable polymer," is a polymer (1) with repeating backbone units having at least some bonds that are unstable under physiological conditions, i.e., in the presence of water, enzymes or other cellular processes, the polymer is biodegradable and (2) the polymer as a whole or its degradation products are capable of being taken up and/or assimilated in vivo or under physiological conditions by any mechanism (including by absorption, solubilization, capillary action, osmosis, chemical action, enzymatic action, cellular action, dissolution, disintegration, erosion and the like, or any combination of these processes) in a subject on a physiologically-relevant time scale consonant with the intended biological use of the polymer.

Resorbable polymers contain cleavable backbone bonds, that when broken, produce smaller fragments, which themselves may be polymeric or monomeric. These smaller fragments are or can be further degraded to become water soluble or to a size that can be engulfed by a macrophage, processed by a cell or otherwise removed from the cellular milieu or tissues at the physiological site of use, resulting in complete or substantially complete degradation and loss of the polymer (i.e., resorption) from the original implantation site. Resorption, for example, can be assessed by measuring mass loss or weight loss of the polymer under physiological conditions by methods known in the art.

When resorbable polymers become completely or substantially resorbed, then the polymer (but not necessarily the monomeric repeating units thereof or smaller polymeric fragments thereof) is no longer present or no longer readily detectable in the subject. For example, if the polymer is a coating on an implanted medical device, the polymer would no longer be present on or detectable on the device. Of course, partial resorption may also be observed, especially if assessed in an early phase of the resorption process. Similarly, if the polymer is formed into a medical device (e.g., suture material, a staple, a device covering, an implant, a plug) or a sustained-release composition (e.g., a drug formulation or vaccine carrier), then the device or composition may no longer be present or detectable at the physiological site of use.

The time scale of resorption depends upon the intended use. The polymers of the invention can be manipulated to provide for rapid resorption under physiological conditions, e.g., within a few days, to longer periods, such as weeks or months or years. Medically-relevant time periods depend upon the intended use and include, e.g., from 1-30 days, 30-180 days and from 1 to 24 months, as well as all time in between such as 5 days, 1, 2, 3, 4, 5 or 6 weeks, 2, 3, 4, 6 or months and the like. Accordingly, the present invention includes biocompatible, biodegradable polymers capable of resorption under physiological condition on medically-relevant time scales, based on appropriate choice of the groups, R, $R_1$, $R_2$ and like.

Hence, the polymers of the invention comprise one or more aminophenol-diacid repeating units represented by the formula

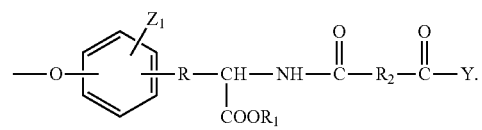

wherein the variables are defined as above and the group C(O)—$R_2$—C(O)— when taken with the nitrogen and oxygen in the backbone, forms the ester and amide bonds of the polyesteramide backbone of the polymer. The oxygen attached to the aromatic ring can be in the ortho, meta or para position relative to the R group on the aromatic ring and is preferably in the para position.

More specifically, R is —$(CR_3R_4)_a$— or —$CR_3$=$CR_4$—, where a is from 0 to 10. If a is zero, then R is a bond. Each $R_3$ and $R_4$ is independently a hydrogen or a linear or branched lower alkyl group having from 1 to 10 carbon atoms. For example, if $R_3$ and $R_4$ are both hydrogen and a is 2, then that moiety is ethylene. In particular embodiments, the R groups include, but are not limited to, a bond, methylene, ethylene, propylene and butylene.

$R_1$ is hydrogen; saturated or unsaturated alkyl, aryl, aryl esters, alkylaryl or alkyl ether having from 1 to 20 carbon atoms; or —$(R_5)_qO((CR_3R_4)_rO)_s$—$R_6$, the latter moiety forming alkylene oxides.

In particular embodiments, the $R_1$ groups are hydrogen, methyl, ethyl, propyl, butyl (including t-butyl), hexyl, allyl, benzyl, and alkylene oxides (e.g., PEGs). When $R_1$ is an aryl ester, then the substituent can be a paraben, including methyl paraben, ethyl paraben, propyl paraben and the like. Another aryl ester is desaminotyrosyl ester, e.g., desaminotyrosyl methyl ester, desaminotyrosyl ethyl ester and the like.

When $R_1$ is an alkylene oxide, that group can be represented by the formula —$(R_5)_qO((CR_3R_4)_rO)_s$—$R_6$, (with r, q, s, $R_3$, $R_4$, $R_5$ and $R_6$ as defined herein). These formulas includes polyethylene glycol chains (PEG) such as —$CH_2O(CH_2CH_2O)_sCH_2$— or —$CH_2CH_2O(CH_2CH_2O)_sCH_2CH_2$— and polypropylene glycol (PPG) chains such as —$CH_2CH_2CH_2O(CH_2CH_2CH_2O)_sCH_2CH_2CH_2$— and the like. Examples of poly(alkylene glycols) include, but are not limited to, PEG, PPG, poly(tetramethylene glycol), PLURONIC® polymers and any derivatives, analogs, homologues, congeners, salts, copolymers and combinations thereof. As is well known, alkylene oxides can be made or are commercially available in a variety of sizes and combinations. For PEGs, the sizes include PEG 200, PEG 400, PEG 600, PEG 1000 and the like. For PLURONIC® polymers, the ratio of polyethylene and polypropylene blocks as well as the overall size can be varied. All such variations are contemplated for use in the present invention.

Overall, the selection of R and $R_1$ determine the nature of the aminophenol moiety. Preferred aminophenol moieties in the polymers of the invention include tyrosine methyl ester (TM), tyrosine ethyl ester (TE), tyrosine benzyl ester (TBz) and tyrosine (T), which are formed when R is $CH_2$ and $R_1$ is, respectively, methyl, ethyl, benzyl or hydrogen. Another aminophenol moiety for the polymers of the invention is 4-hydroxyphenyl glycine and its esters, e.g., PE, PM and PBz.

$R_2$ is independently linear or branched, substituted or unsubstituted alkylene, alkenylene, alkynylene, arylene, alkylarylene, a divalent alkyl ether or aryl ether moiety having from 1 to 30 carbon atoms; —$(R_5)_qO((CR_3R_4)_rO)_s(R_5)_q$—; or —$(R_5)_qCO_2((CR_3R_4)_rO)_sCO(R_5)_q$—. $R_2$ forms part of the diacid moiety, i.e., as —C(O)—$R_2$—C(O)— linked by two amide bonds, two ester bonds or an amide and an ester bond, depending on the method of polymerization.

Hence, $R_2$ is a divalent hydrocarbon group and can be linear or branched, substituted or unsubstituted. Such groups include alkylene, alkenylene, arylene, alkylarylene moieties having from 1 to 30 carbon atoms as well as larger divalent alkylene oxide or arylene oxide moieties (based on the number of repeating units in those groups). As an example, when $R_2$ is a divalent alkylene oxide, that group can be represented by the formula $—(R_5)_qO((CR_3R_4)_rO)_s(R_5)_q—$, (with r, q, s, $R_3$, $R_4$, $R_5$ and $R_6$ as defined herein). This moiety includes polyethylene glycol chains (PEG) such as $—CH_2O(CH_2CH_2O)_sCH_2—$ or $—CH_2CH_2O(CH_2CH_2O)_sCH_2CH_2—$ and polypropylene glycol chains such as $—CH_2CH_2CH_2O(CH_2CH_2CH_2O)_sCH_2CH_2—CH_2—$ and the like. For convenience, these chains are referred to as PEG acids (because of the method of condensing these moieties). Further, $R_2$ can be represented by the formula $—(R_5)_qCO_2((CR_3R_4)_rO)_sCO(R)_q—$, which are referred to as PEG-bis-acids. In a specific embodiment, this formula provides polymers which have PEG bis-succinate as the diacid-based moiety. PEG bis-succinate, taken with the carbonyls of the diacid, is represented by the formula —C(O)CH$_2$CH$_2$C(O)O(CH$_2$CH$_2$O)$_s$C(O)CH$_2$CH$_2$C(O)—, where both $R_5$s are ethylene, and r, $R_3$ and $R_4$ together form an ethylene group. If the formula is the same except that both $R_5$s are n-propylene, then the equivalent moiety is PEG bis-glutarate.

In specific embodiments, the diacid moieties formed with $R_2$ (i.e., as HO—C(O)—$R_2$—C(O)—OH) include oxalic acid, malonic acid, succinic acid, glutaric acid, adipic acid, pimelic acid, suberic acid, azelaic acid, and sebacic acid, as well as diglycolic acid (where $R_2$ is $—CH_2OCH_2—$), dioxaoctanoic acid ($R_2$ is $—CH_2OCH_2CH_2OCH_2—$), alkylene oxide derivatives such as PEG, PEG bis-succinate and the like. In accordance with the invention, these diacids units have amide or ester backbone bonds when polymerized.

$R_3$ and $R_4$ are also present in the groups $—(R_5)_qO((CR_3R_4)_rO)_s(R_5)_q—$ and $(R_5)_qCO_2((CR_3R_4)_rO)_sCO(R_5)_q$, and each $R_3$ and $R_4$ is independently a hydrogen or a linear or branched lower alkyl group having from 1 to 10 carbon atoms. In these functional groups, when $R_3$ and $R_4$ are both hydrogen and r is 2, then that moiety is ethylene and when taken with oxygen forms the repeating ethylene oxide portion of PEG. When $R_3$ and $R_4$ are both hydrogen and r is 3, then taken with the oxygen they form the propylene oxide repeat of PPG. For $—(R_5)_qO((CR_3R_4)_rO)_s(R)_q—$ and $—(R_5)_qCO_2((CR_3R_4)_rO)_nCO(R_5)_q—$, in most embodiments $R_3$ and $R_4$ are hydrogen and r is 2 or 3.

$R_5$, is independently a linear or branched lower alkylene or alkenylene group. In preferred embodiments, $R_5$ is methylene, ethylene or propylene.

$R_6$ is independently linear or branched, substituted or unsubstituted, saturated or unsaturated lower alkyl. In particular embodiments, $R_6$ is methyl, ethyl, propyl, butyl (t-butyl, n-butyl, isobutyl) and the like.

In accordance with the invention, the awl ring of the amino phenol can have from zero to four $Z_1$ or $Z_2$ substituents. If the valence of a position on the aromatic ring is not otherwise filled, then that position has a hydrogen atom. $Z_1$ or $Z_2$ are each independently selected from the group consisting of a halide, a lower alkyl, an alkoxy, a nitro, an alkylether, a protected hydroxyl, a protected amino and a protected carboxylic acid group.

When at least one of $Z_1$ or $Z_2$ is present and is bromine or iodine, then the polymer is radioopaque and has the uses described in U.S. Pat. No. 6,475,477. For example, use of radioopaque medical devices allows non-invasive techniques to monitor the presence and/or disappearance of the device, including the biodegradation and resorption of the device (for devices that are fully resorbable). Similarly, radioopaque microspheres formed from polymers of the invention may be useful as imaging agents or for drug delivery, and again can be monitored with non-invasive techniques such as x-ray, CAT scan, and the like.

Such polymers can be prepared from aminophenol moieties that have been halogenated prior to polymerization using standard halogenation reactions. While such reactions may tend to have preferred positions for the halogen atom on the aromatic ring (e.g., ortho), it is contemplated that the halogen atom can be at any available position.

$Z_1$ can also be a protected hydroxyl, protected amine or protected carboxylic group. In addition to the uses of the invention, in some instances, polymers having such protected substituents can be used as intermediates to prepare other polymers of the invention. Protecting groups for OH, $NH_2$ and COOH groups are well known in the art and any are suitable for use in accordance with the invention, provided they are stable and compatible with the synthetic methods used to produce the polymers of the invention. Because of the bifunctionality of the aminophenol and the diacid, the basic monomeric unit (here arbitrarily designated as repeat a), can add either another of repeat a or add repeat b as the subsequent monomeric unit. Accordingly, the variable Y reflects this and is defined as repeat a with the amide bond (below left) or repeat b with the ester bond (below right).

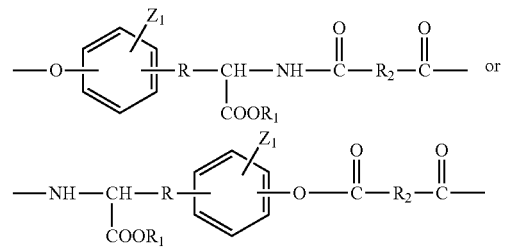

For a random polymer each subsequent Y would be randomly either "repeat a" or "repeat b." For a strictly alternating $(a)_n$ polymer, Y would always be "repeat a." For a strictly alternating $(ab)_n$, polymer, Y would always be "repeat b." In addition, each $R_2$ can be the same or different, depending upon the type of polymer and the number of different diacid monomers employed.

The value of each a is independently 0 or one of the whole numbers 1-10. When a is zero, the corresponding group is omitted and a single carbon bond is present. The value of each q and r is independently one of the whole numbers 1, 2, 3 or 4.

The value of each s is independently about 1 to about 5000 and determines the number of repeat units in the alkylene oxide chain. Hence, s can range from 1 or from 5 to about 10, to about 15, to about 20, to about 30, to about 40, to about 50, to about 75, to about 100, to about 200, to about 300, to about 500, to about 1000, to about 1500, to about 2000, to about 2500, to about 3000, to about 4000 and to about 5000. Additionally, when the length of the alkylene oxide chain is stated as a molecular weight, such as with PEG 200, PEG 400, PEG 600 and the like, then s need not be a whole number but can also be expressed as a fractional value, representative of the average number of alkylene oxide repeating units based on the cited (or a measured) molecular weight of the poly(alkylene oxide).

Thus, in one embodiment, the polymers of the present invention include polymers of structure A:

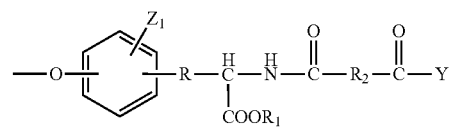

wherein $Z_1$ is H, R is —$CH_2$—, $R_1$ is a lower alkyl, and Y is:

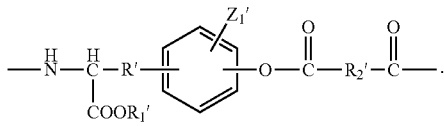

wherein $R_2$ and $R_2'$ are the same; R' is —$(CR_3R_4)_a$— or —$CR_3$=$CR_4$—; $R_1'$ is hydrogen, lower alkyl, or benzyl; $Z_1'$ is halide, lower alkyl, alkoxy, nitro, alkyl ether, a protected hydroxyl group, a protected amino group or a protected carboxylic acid group; and $R_2'$ is a divalent, linear or branched, substituted or unsubstituted alkylene, alkenylene, alkynylene, arylene, alkylarylene, alkyl ether or aryl ether moiety having from 1 to 30 carbon atoms; —$(R_5)_qO((CR_3R_4)_rO)_s(R_5)_q$—; or —$(R_5)_qCO_2((CR_3R_4)_rO)_nCO(R_5)_q$—.

In another embodiment, the polymers of the present invention include polymers of structure A:

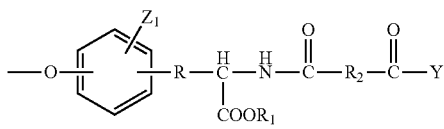

wherein $Z_1$ is H, R is —$CH_2$—, $R_1$ is a lower alkyl, and Y is:

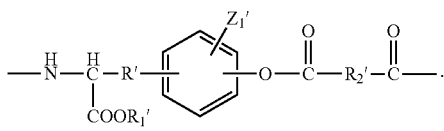

wherein $R_2$ and $R_2'$ are different; R' is —$(CR_3R_4)_a$— or —$CR_3$=$CR_4$—; $R_1'$ is hydrogen, lower alkyl, or benzyl; $Z_1'$ is halide, lower alkyl, alkoxy, nitro, alkyl ether, a protected hydroxyl group, a protected amino group or a protected carboxylic acid group; and $R_2'$ is a divalent, linear or branched, substituted or unsubstituted alkylene, alkenylene, alkynylene, arylene, alkylarylene, alkyl ether or aryl ether moiety having from 1 to 30 carbon atoms; —$(R_5)_qO((CR_3R_4)_rO)_s(R_5)_q$—; or —$(R_5)_qCO_2((CR_3R_4)_rO)_sCO(R_5)_q$—.

In another embodiment, the polymers of the present invention include polymers of structure A

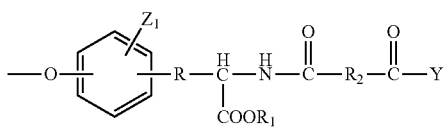

wherein $Z_1$ is H, R is —$CH_2$—, $R_1$ is a lower alkyl, and Y is:

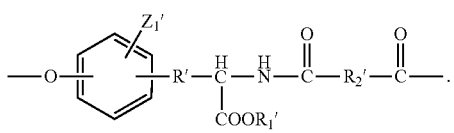

wherein $R_2$ and $R_2'$ are the same; R' is —$(CR_3R_4)_a$— or —$CR_3$=$CR_4$—; $R_1'$ is hydrogen, lower alkyl, or benzyl; $Z_1'$ is halide, lower alkyl, alkoxy, nitro, alkyl ether, a protected hydroxyl group, a protected amino group or a protected carboxylic acid group; and $R_2'$ is a divalent, linear or branched, substituted or unsubstituted alkylene, alkenylene, alkynylene, arylene, alkylarylene, alkyl ether or aryl ether moiety having from 1 to 30 carbon atoms; —$(R_5)_qO((CR_3R_4)_rO)_s(R_5)_q$—; or —$(R_5)_qCO_2((CR_3R_4)_rO)_sCO(R_5)_q$—.

In another embodiment, the polymers of the present invention include polymers of structure A:

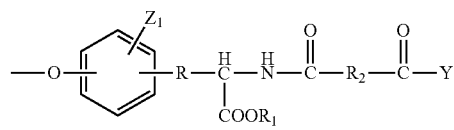

wherein $Z_1$ is H, R is —$CH_2$—, $R_1$ is a lower alkyl, and Y is:

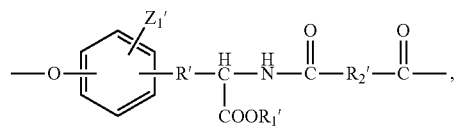

wherein $R_2$ and $R_2'$ are different; R' is —$(CR_3R_4)_a$— or —$CR_3$=$CR_4$—; $R_1'$ is hydrogen, lower alkyl, or benzyl; $Z_1'$ is halide, lower alkyl, alkoxy, nitro, alkyl ether, a protected hydroxyl group, a protected amino group or a protected carboxylic acid group; and $R_2'$ is a divalent, linear or branched, substituted or unsubstituted alkylene, alkenylene, alkynylene, arylene, alkylarylene, alkyl ether or aryl ether moiety having from 1 to 30 carbon atoms; —$(R_5)_qO((CR_3R_4)_rO)_s(R_5)_q$—; or —$(R_5)_qCO_2((CR_3R_4)_rO)_sCO(R_5)_q$—.

In still other embodiments, the polymers of the present invention include polymers of structure A:

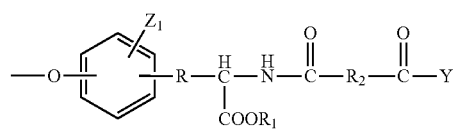

wherein $Z_1$ is H, R is —$CH_2$—, $R_1$ is a lower alkyl, and Y is:

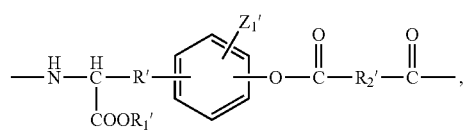

wherein $R_2$ and $R_2'$ are the same, and are independently selected from —$CH_2$—O—$CH_2$—, —$CH_2CH_2CH_2$—, —$CH_2CH_2$—; R' is —$(CR_3R_4)_a$— or —$CR_3$=$CR_4$—; $R_1'$ is hydrogen, lower alkyl, or benzyl; $Z_1'$ is halide, lower alkyl, alkoxy, nitro, alkyl ether, a protected hydroxyl group, a protected amino group or a protected carboxylic acid group; and $R_2'$ is a divalent, linear or branched, substituted or unsubstituted alkylene, alkenylene, alkynylene, arylene, alkylarylene, alkyl ether or aryl ether moiety having from 1 to 30 carbon atoms; —$(R_5)_qO((CR_3R_4)_rO)_s(R_5)_q$—; or —$(R_5)_qCO_2((CR_3R_4)_rO)_sCO(R_5)_q$—.

In still other embodiments, the polymers of the present invention include polymers of structure A:

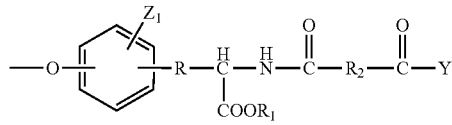

wherein $Z_1$ is H, R is —$CH_2$—, $R_1$ is a lower alkyl, and Y is:

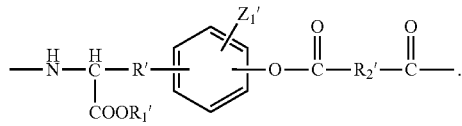

wherein $R_2$ and $R_2'$ are different, and are independently selected from —$CH_2$—O—$CH_2$—, —$CH_2CH_2CH_2$—, —$CH_2CH_2$—; $R_1'$ is hydrogen, lower alkyl, or benzyl; $Z_1'$ is halide, lower alkyl, alkoxy, nitro, alkyl ether, a protected hydroxyl group, a protected amino group or a protected carboxylic acid group; and $R_2'$ is a divalent, linear or branched, substituted or unsubstituted alkylene, alkenylene, alkynylene, arylene, alkylarylene, alkyl ether or aryl ether moiety having from 1 to 30 carbon atoms; —$(R_5)_qO((CR_3R_4)_rO)_s(R_5)_q$—; or —$(R_5)_qCO_2((CR_3R_4)_rO)_sCO(R_5)_q$—.

In still other embodiments, the polymers of the present invention include polymers of structure A:

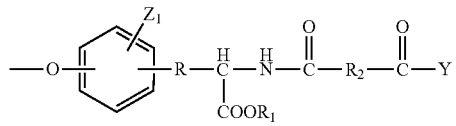

wherein $Z_1$ is H, R is —$CH_2$—, $R_1$ is a lower alkyl, and Y is:

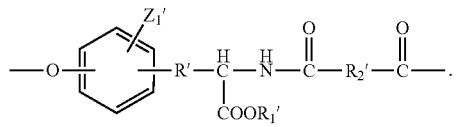

wherein $R_2$ and $R_2'$ are the same, and are independently selected from —$CH_2$—O—$CH_2$—, —$CH_2CH_2CH_2$—, —$CH_2CH_2$—; $R_1'$ is hydrogen, lower alkyl, or benzyl; $Z_1'$ is halide, lower alkyl, alkoxy, nitro, alkyl ether, a protected hydroxyl group, a protected amino group or a protected carboxylic acid group; and $R_2'$ is a divalent, linear or branched, substituted or unsubstituted alkylene, alkenylene, alkynylene, arylene, alkylarylene, alkyl ether or aryl ether moiety having from 1 to 30 carbon atoms; —$(R_5)_qO((CR_3R_4)_rO)_s(R_5)_q$—; or —$(R_5)_qCO_2((CR_3R_4)_rO)_sCO(R_5)_q$—.

In still other embodiments, the polymers of the present invention include polymers of structure A:

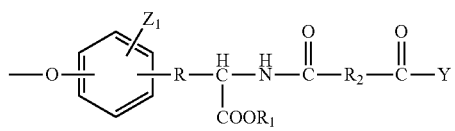

wherein $Z_1$ is H, R is —$CH_2$—, $R_1$ is a lower alkyl, and Y is:

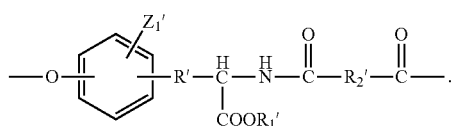

wherein $R_2$ and $R_2'$ are different, and are independently selected from —$CH_2$—O—$CH_2$—, —$CH_2CH_2CH_2$—, —$CH_2CH_2$—; $R_1'$ is hydrogen, lower alkyl, or benzyl; $Z_1'$ is halide, lower alkyl, alkoxy, nitro, alkyl ether, a protected hydroxyl group, a protected amino group or a protected carboxylic acid group; and $R_2'$ is a divalent, linear or branched, substituted or unsubstituted alkylene, alkenylene, alkynylene, arylene, alkylarylene, alkyl ether or aryl ether moiety having from 1 to 30 carbon atoms; —$(R_5)_qO((CR_3R_4)_rO)_s(R_5)_q$—; or —$(R_5)_qCO_2((CR_3R_4)_rO)_sCO(R_5)_q$—.

Examples of particular polymers according to the present invention are shown below, in Table 2:

TABLE 2

| | Y | |
|---|---|---|
| TE-diglycolate-TE Glutarate | $Z_1$ = H<br>R = $CH_2$<br>$R_1$ = $CH_2$—$CH_3$<br>$R_2$ = $CH_2$—O—$CH_2$ | $Z_1$ = H<br>R = $CH_2$<br>$R_1$ = $CH_2$—$CH_3$<br>$R_2$ = $CH_2$—$CH_2$—$CH_2$ |
| TE-glutarate-TE glutarate | $Z_1$ = H<br>R = $CH_2$<br>$R_1$ = $CH_2$—$CH_3$<br>$R_2$ = $CH_2$—$CH_2$—$CH_2$ | $Z_1$ = H<br>R = $CH_2$<br>$R_1$ = $CH_2$—$CH_3$<br>$R_2$ = $CH_2$—$CH_2$—$CH_2$ |
| TE-succinate-TE glutarate | $Z_1$ = H<br>R = $CH_2$<br>$R_1$ = $CH_2$—$CH_3$<br>$R_2$ = $CH_2CH_2$ | $Z_1$ = H<br>R = $CH_2$<br>$R_1$ = $CH_2$—$CH_3$<br>$R_2$ = $CH_2CH_2$—$CH_2$ |

TABLE 2-continued

| Y |
|---|
| 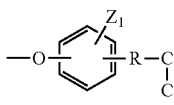 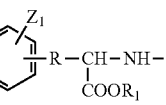 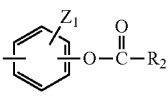 |

| | | |
|---|---|---|
| TE-glutarate-TE succinate | $Z_1 = H$<br>$R = CH_2$<br>$R_1 = CH_2$—$CH_3$<br>$R_2 = CH_2CH_2$—$CH_2$ | $Z_1 = H$<br>$R = CH_2$<br>$R_1 = CH_2$—$CH_3$<br>$R_2 = CH_2CH_2$ |
| TE-diglycolate-TE<br>(25% peg 600 acid/75%<br>glutaric acid) | $Z_1 = H$<br>$R = CH_2$<br>$R_1 = CH_2$—$CH_3$<br>$R_2 = CH_2$—O—$CH_2$ | $Z_1 = H$<br>$R = CH_2$<br>$R_1 = CH_2$—$CH_3$<br>$R_2 = CH_2CH_2$—$CH_2$ (75%) =<br>$CH_2$—O—$(CH_2$—$CH_2$—O$)_{10-12}$—$CH_2$ (25%) |
| TE-diglycolate-TE<br>(27.5% peg 600<br>acid/72.5% glutaric acid) | $Z_1 = H$<br>$R = CH_2$<br>$R_1 = CH_2$—$CH_3$<br>$R_2 = CH_2$—O—$CH_2$ | $Z_1 = H$<br>$R = CH_2$<br>$R_1 = CH_2$—$CH_3$<br>$R_2 = CH_2CH_2$—$CH_2$ (72.5%) =<br>$CH_2$—O—$(CH_2$—$CH_2$—O$)_{10-12}$—$CH_2$ (27.5%) |
| TE-diglycolate-TE (25%<br>PEG 400 bissuccinate/<br>75% succinate) | $Z_1 = H$<br>$R = CH_2$<br>$R_1 = CH_2$—$CH_3$<br>$R_2 = CH_2$—O—$CH_2$ | $Z_1 = H$<br>$R = CH_2$<br>$R_1 = CH_2$—$CH_3$<br>$R_2 = CH_2CH_2$ (75%) =<br>$CH_2$—$CH_2$—COO—$(CH_2$—$CH_2$—O$)_{8-10}$—CO—$CH_2$—$CH_2$<br>(25%) |
| TE-diglycolate-TE (25%<br>PEG 400 bissuccinate/<br>75% glutarate) | $Z_1 = H$<br>$R = CH_2$<br>$R_1 = CH_2$—$CH_3$<br>$R_2 = CH_2$—O—$CH_2$ | $Z_1 = H$<br>$R = CH_2$<br>$R_1 = CH_2$—$CH_3$<br>$R_2 = CH_2CH_2$ (75%) =<br>$CH_2$—$CH_2$—COO—$(CH_2$—$CH_2$—O$)_{8-10}$—CO—$CH_2$—$CH_2$<br>(25%) |
| TE-diglycolate-TE (25%<br>PEG 400 bissuccinate/<br>75% adipate) | $Z_1 = H$<br>$R = CH_2$<br>$R_1 = CH_2$—$CH_3$<br>$R_2 = CH_2$—O—$CH_2$ | $Z_1 = H$<br>$R = CH_2$<br>$R_1 = CH_2$—$CH_3$<br>$R_2 = CH_2CH_2$—$CH_3$ (75%) =<br>$CH_2$—$CH_2$—COO—$(CH_2$—$CH_2$—O$)_{8-10}$—CO—$CH_2$—$CH_2$<br>(25%) |
| TE-diglycolate-TE (35%<br>PEG 400 bissuccinate/<br>65% adipate) | $Z_1 = H$<br>$R = CH_2$<br>$R_1 = CH_2$—$CH_3$<br>$R_2 = CH_2$—O—$CH_2$ | $Z_1 = H$<br>$R = CH_2$<br>$R_1 = CH_2$—$CH_3$<br>$R_2 = CH_2CH_2$—$CH_2$ (65%) =<br>$CH_2$—$CH_2$—COO—$(CH_2$—$CH_2$—O$)_{8-10}$—CO—$CH_2$—$CH_2$<br>(35%) |
| TE-15T glutarate | $Z_1 = H$<br>$R = CH_2$<br>$R_1 = CH_2$—$CH_3$ (85%)<br>$R_2 = CH_2CH_2$—$CH_2$ | $Z_1 = H$<br>$R = CH_2$<br>$R_1 = H$ (n%)<br>$R_2 = CH_2CH_2$—$CH_2$ | $Z_1 = H$<br>$R = CH_2$<br>$R_1 = H$ (15%-n)<br>$R_2 = CH_2CH_2$—$CH_2$ |

The polymers of the invention can be homopolymers or copolymers. To create heteropolymers (or copolymers), as also described above in context of polymer nomenclature, mixtures of the aminophenol and/or the diacid (or appropriate starting materials) can be used to synthesize the polymers of the invention.

When the polymers are copolymers, they contain from at least about 0.01% to 100% of the repeating monomer units, from at least about 0.05, 0.1, 0.5, 1, 2, 3, 4, 5, 6, 8, 10, 12, 15% to about 30, 40, 50, 60, 75, 90, 95 or 99% in any combination of ranges. In certain embodiments, the range of repeating units in free acid form on the aminophenol moiety of the polymer is from about 5 to about 50% (i.e., $R_1$ is H-prepared via an intermediate in which $R_1$ is benzyl, and the benzyl is subsequently removed by conventional synthetic methods, e.g., hydrogenolysis), with the remaining $R_1$ groups being alkyl or other ester stable to hydrogenolysis. For those polymers, preferred ranges of free acid are from about 10 to about 30%, and more preferably from about 10 or about 15%.

Alternatively or additionally, the copolymers can have varying ratios of the diacid moiety, so that mixtures have from about 20% to about 80% of at least one diacid described herein, and preferably are mixture of two or more diacids described herein. Preferred mixed diacids are combinations of various alkylene oxide type moieties, such as PEG acids or PEG-bis-alkyl acids or combinations of those alkylene oxide type moieties with other diacids, especially small, and preferably but not necessarily, naturally-occurring diacids such as succinic acid, glutaric acid, adipic acid and diglycolic acid. For alkylene oxide mixtures, the mixture contains from about 20, 25, 30, 35, 40, 45 to about 50% of one alkylene oxide, and in many embodiments about 50% of each alkylene oxide. For alkylene oxide-other diacid mixtures, the mixture contains from about 20, 25, 30, 35, 40, 45 or 50% of the alkylene oxide, with the remainder being the other diacid. For these combinations, the amount of the alkylene oxide in most embodiments is about 20 to about 40%.

Further, the ester moiety of the aminophenol can be varied by using alkyl esters or another class of esters such as alkylaryl esters, or esters with alkylene oxide chains or ether chains, or another compatible functional group. To have this ester moiety converted to a free acid, the polymer can be synthesized using a benzyl ester (or other easily hydrolyzable moiety) which can be removed by hydrogenolysis as described in U.S. Pat. No. 6,120,491 or by other technique that preferentially removes the benzyl group without hydrolyzing the backbone of the polymer. Hence, the polymers of the invention can be made with mixtures aminophenol and diacids that have variability among the different substituents, i.e., differences can reside at any of R, $R_1$-$R_{10}$, $Z_1$ or the other variables of the repeat units. Finally, the other monomer units in the copolymer can be substantially different provided such moieties preserve the properties of the polymer and are capable of copolymerizing to form polymers with aminophenol and diacid moieties.

Breakdown of the polymers of the invention can be assessed in a variety of ways using in vitro or in vivo methods known in the art. It may be useful to mimic the in vivo degradation by in vitro methods. For example, aging a polymer-coated device (or a composition or device formed primarily from a polymer of the invention) at 37° C. in phosphate buffered saline (PBS) at pH 7.4 may reproduce the hydrolytic degradation process. Mass loss can be assessed in vitro using weight loss measurements for pieces of the device, films of polymer or other relevant material that have been placed in PBS at 37° C. or in vivo by implanting materials subcutaneously in a suitable porous container so that the polymer is exposed to body fluids. Periodic removal of the device from the physiological medium or explant container, followed by drying and weighing produces information related to the mass loss of the material. Molecular weight loss can be measured by assessing the molecular weight at predetermined time points from samples explanted, dried, and subjected to GPC to determine the molecular weight. The identities of the breakdown products can also be determined by art know methods. Further, as needed, in vivo animal models can be used to correlate in vivo and in vitro degradation behavior.

Synthesis:

The polymers of the invention can be synthesized by a variety of methods using techniques known in the polymer chemistry art. Four methods are described below, but variations of these methods will be within the knowledge of the skilled artisan.

The first of these methods provides strictly alternating $(ab)_n$ polymers by synthesizing a trimeric diol and condensing that diol with a diacid to produce the desired polymers. The first step is done under conditions that favor amide bond formation over ester bond formation, for example by using a mild coupling agent such as HOBT (hydroxybenzotriazole). Hence, the monomers are reacted to produce the trimer HO-AP-NH$_2$+HO—C(O)—R$_{2a}$—C(O)OH→HO-AP-NH—C(O)—R$_{2a}$—C(O)—NH-AP-OH.

The trimer can also be represented by the structure shown below:

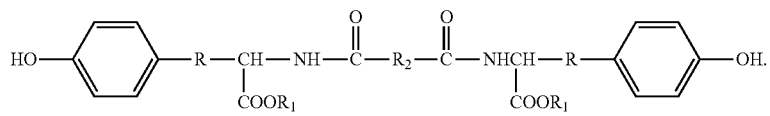

The trimer is purified and reacted with a second diacid, HO—C(O)—R$_{2b}$—C(O)OH, using a stronger coupling reagent such as DPTS (4-dimethylaminopyridinium 4-toluenesulfonate) to yield the strictly alternating repeat unit shown below:

[O-AP-NH—C(O)—R$_{2a}$—C(O)—NH-AP-O—C(O)—R$_{2b}$—C(O)]

The second method also produces strictly alternating polymers $(ab)_n$ polymers by synthesizing first synthesizing a trimer with protected amines. This is accomplished by coupling an amine-protected aminophenol with a diacid, isolating the resultant trimer with protected amines at each end, deprotecting the amines and reacting with a second diol under condensation conditions. For example, HO-AP—NHY and HO—C(O)—R$_{2a}$—C(O)OH are coupled to make YHN-AP—O—C(O)—R$_{2a}$—C(O)—O-AP-NHY, where Y is a protecting group that can be removed in the presence of the ester bonds in the trimer and AP is a shorthand for the remainder of the aminophenol structure other than the hydroxyl and amine groups. After deprotection, a second diacid, HO—C(O)—R$_{2b}$—C(O)OH, is used to polymerize this trimer to form the strictly alternating $(ab)_n$ polymers.

The third method produces strictly alternating $(a)_n$ polymers by reacting the aminophenol with an anhydride to produce a dimer with free OH and free COOH groups as drawn in the exemplary reaction scheme below:

HO-AP-NH$_2$+R$_2$C(O—(O)—R$_2$→HO-AP'NH—C(O)—R$_2$—COOH.

The reaction product is purified, more coupling reagent added to allow self condensation to proceed and produce a polymer with in which the diacid has an amide bond on one side and an ester bond on the other side as shown schematically below:

—(—O-AP-NH—C(O)—R$_2$—C(O)—)(—O-AP-NH—C(O)—R—C(O)—)(—O-AP-NH—C(O)—R$_2$—C(O)—)—.

The fourth synthesis method produces a random copolymer of the aminophenol and the diacid. In this method, equimolar amounts of each compound are reacted in the presence of a coupling reagent, preferably a strongly reactive coupling reagent, and catalyst as described, for example, in U.S. Pat. Nos. 5,216,115; 5,317,077; 5,587,507; 5,670,602; 6,120,491; RE37,160E; and RE37,795E as well as in the literature, other patents and patent applications. Those of skill in the art can readily adapt these procedures to synthesize the polymers of the present invention. These polymers generally have low to moderate molecular weights (30-60 kDa).

The polymers and synthetic intermediates can be purified by those of skill in the art using routine methods, including extraction, precipitation, filtering, recrystallization and the like.

Examples of coupling agents for the methods described above include, but are not limited to, EDCI.HCl (1-ethyl-3-(3-dimethylaminopropyl)carbodiimide hydrochloride), DCC (dicyclohexylcarbodiimide), DIPC (diisopropylcarbodiimide) in combination with DPTS, PPTS (pyridinium tosylate), DMAP (4-dimethylaminopyridine). The use of EDCI.HCl is preferred for producing the trimer in the first step for the first synthesis method described above. Suitable solvents include, but are not limited to methylene chloride, chloroform, 1,2-dichloroethane, either neat or in combination with lesser quantities of NMP or DMF.

Accordingly, the first method of synthesis described above, provides a method of the invention directed to a method of synthesizing a strictly alternating PEA polymer that is at least 40-100% higher in molecular weight than the corresponding random polymer by reacting about two equivalents of an aminophenol and about one equivalent of a first diacid with a coupling agent for a time and under conditions to preferentially form amide bonds and produce an aminophenol-diamide-aminophenol trimer; recovering the trimer and further reacting it with a about one equivalent of a second diacid in the presence of a second coupling agent for a time and under conditions to form said PEA polymer and recovering the polymer. This synthesis method allows one to easily vary the diacids and aminophenols in the PEA polymer in a predictable structural manner.

In this method, the first coupling reaction is conducted under conditions to favor amide bond formation. Such conditions employ mild coupling conditions and use weaker coupling reagents. A particularly useful coupling reagent for this step is EDCI.HCl with the co-catalyst HOBt in organic solvent. Reaction times should be chosen to allow the reaction to near or go to completion, i.e., until no or little further molecular weight gain appears in the polymer. Typical reaction times vary from at least overnight (12-16 h) to about (24 to 48 h) and can be readily determined by those of skill in the art. Reaction temperatures can also be readily determined by those of skill in the art. In the second coupling reaction (after isolation of the trimer), a stronger coupling agent is used to drive ester bond formation. In some cases, after the reaction has proceeded for a time, the second reaction achieves additional molecular weights gains by spiking the reaction with a small additional amount (1-10%) of the second diacid.

In this method the first and second diacids can be the same or different, and either diacid can comprise a mixture of two or more different diacids. Similarly, mixtures of the trimer can be used. Examples of useful coupling agents and solvents are described above and in the Examples.

Uses:

The polymers of the invention have a myriad of biological uses when a biocompatible, biodegradable polymer is needed, for coating medical devices, to form fully or partially resorbable medical devices, to deliver drugs in specific manners (either in conjunction with such device or as part of a pharmaceutical composition comprising the polymer, a drug and other agents. It should be understood that the polymers are useful without the presence of drugs. For example, a polymer coating on a surgical mesh can increase mesh stiffness, and thereby allow easier handling at the time of implantation yet still provide a mesh that softens over time and is comfortable for the patient. Moreover, a polymer-coated, flat mesh can be formed into a three dimensional shape, and this can be useful in surgical repairs. Fully resorbable devices can be used as sutures intended to impart strength for a period before dissolving, as temporary wound closures, such as a femoral plug, and the like.

Further uses for the polymers of the invention are described in detail, for example, in U.S. Ser. No. 11/672,929, filed Feb. 8, 2007 which describes coated surgical meshes for a variety of applications; in U.S. Ser. No. 60/864,597, filed Nov. 6, 2006 which describes fully and partially resorbable coverings, pouches, bags and coated meshes for cardiac rhythm management devices, neurostimulators as well as for other implantable medical devices; and in U.S. Ser. No. 60/908, 960, filed Mar. 29, 2007 for resorbable coverings for breast implants.

The compositions of the present invention can be used to form medical articles and coatings (i) that have sufficient mechanical properties for applications that can benefit from biodegradable polymers, (ii) that can release agents substantially free of additional molecules derived from a polymeric carrier, (iii) that can be designed to have a predetermined release rate and resorption rate; and (iv) that can be combined with drugs that are not only bioactive and/or biobeneficial but also control a physical property and/or a mechanical property of a medical article or coating formed from the polymer.

Blends:

An additional way to manipulate drug release and resorption characteristics is to blend polymers. Accordingly, the present invention provides blends of the polymers of the invention with other biocompatible polymers, for example other biodegradable polymers. These other polymers include, but are not limited to, polylactic acid, polyglycolic acid and copolymers and mixtures thereof such as poly(L-lactide) (PLLA), poly(D,L-lactide) (PLA)polyglycolic acid [polyglycolide (PGA)], poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), poly(D,L-lactide-co-caprolactone) (PLA/PCL) and poly(glycolide-co-caprolactone) (PGA/PCL); poly(oxa)esters, polyethylene oxide (PEO), polydioxanone (PDS), polypropylene fumarate, poly (ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly(phosphazene), poly(phosphate ester), poly(amino acid), polydepsipeptides, maleic anhydride copolymers, polyiminocarbonates, poly[(97.5% dimethyl-trimethylene carbonate)-co-(2.5% trimethylene carbonate)], poly(orthoesters), other tyrosine-derived polyarylates, other tyrosine-derived polycarbonates, other tyrosine-derived polyiminocarbonates, other tyrosine-derived polyphosphonates, polyethylene oxide, polyethylene glycol, polyalkylene oxides, hydroxypropylmethylcellulose, polysaccharides such as hyaluronic acid, chitosan and regenerate cellulose, and proteins such as gelatin and collagen, and mixtures and copolymers thereof, among others as well as PEG derivatives or blends of any of the foregoing.

Using blends provides many advantages, including the ability to make partially resorbable devices and fully resorbable devices that have varied resorption times for parts or all of the device. For example, a partially resorbable device may increase porosity over time and thus permit tissue in growth. Those of skill in the art can readily pick combinations of polymers to blend and determine the amounts of each polymer need in the blend to produce a particular product or achieve a particular result.

Drugs:

In most embodiments, one or more drug, biological agent, or active ingredient that is compatible with the polymers, monomers and blends of the invention can be incorporated in, formed into or used in conjunction or combination with a pharmaceutical composition or a medical device coated or formed from the polymers, monomers or blends of the invention ("compatible" means that the drug does not degrade the polymer, and the polymer does not degrade the drug). Doses for such drugs and agents are known in the art and are used in therapeutically-effective amounts. In addition to measuring polymer degradation and resorption, those of skill in the art can monitor drug release using the same techniques as well as others. For example, antibiotic activity can be measured by zone of inhibition assays, pain relief can be measured in animal models for pain and more.

In accordance with the invention, drugs and biologically-active agents include, but are not limited to, anesthetics, antimicrobials (which include antibiotics, antifungal agents and antibacterial agents), anti-inflammatory agents, fibrosis-inhibiting agents, anti-scarring agents, cell growth inhibitors, growth factors and the like.

As used herein, the term "drug" or "drugs" is used to include all types of therapeutic agents, whether small molecules or large molecules such as proteins, nucleic acids and the like. The drugs of the invention can be used alone or in combination.

As used herein, "therapeutically-effective amount" refers to that amount of a drug or bioactive agent necessary to administer to a host to achieve a desired therapeutic effect in treating, ameliorating or preventing a disease or condition. For example, a therapeutically-effective amount can be that amount to provide antimicrobial activity, pain relief, anti-inflammatory activity, antifibrotic activity, anti-tumor or cancer activity and the like associated with the particular drug or biological agent in use. Potentially therapeutically-effective amounts for known drugs are available in the literature or can be determined, for new or known drugs, using art known methods, techniques and standards.

Examples of non-steroidal anti-inflammatory agents include, but are not limited to, acetaminophen, aspirin, celecoxib, diclofenac, diflunisal, flurbiprofen, ibuprofen, indomethacin, ketoprofen, ketorolac, meclofenamate, meloxicam, methyl salicylate, nabumetone, naproxen, oxaprozin, piroxicam, sulindac, tolmetin and trolamine.

Examples of anesthetics include, but are not limited to, lidocaine, bupivacaine, mepivacaine and xylocalne. Local anesthetics have weak antibacterial properties and can play a dual role in the prevention of acute pain and infection.

Examples of antimicrobial drugs include, but are not limited to aminoglycosides such as amikacin, gentamicin, kanamycin, neomycin, streptomycin, and tobramycin; antibiotics such as bacitracin, clindamycin, daptomycin, lincomycin, linezolid, metronid, polymyxin, rifaximin, vancomycin; cephalosporins such as cephazolin; macrolide antibiotics such as erythromycin, azithromycin and the like; 13-lactam antibiotics such as penicillins; quinolones such as ciprofloxacin; sulfonamides such as sulfadiazine; tetracyclines such as minocycline and tetracycline; and other antibiotics such as rifampin, triclosan, chlorhexidine, sirolimus and everolimus.

Other drugs that can be used include, but are not limited to, keflex, acyclovir, cephradine, malphalen, procaine, ephedrine, adriamycin, daunomycin, plumbagin, atropine, quinine, digoxin, quinidine, biologically active peptides, cephradine, cephalothin, cis-hydroxy-L-proline, melphalan, penicillin V, nicotinic acid, chemodeoxycholic acid, chlorambucil and anti-neoplastic agents such as paclitaxel, sirolimus, 5-fluorouracil and the like. Examples of useful proteins include cell growth inhibitors such as epidermal growth factor antagonists.

Preferred antimicrobial agents of the invention include rifampin, minocycline, gentamicin, vancomycin, triclosan, sirolimus and everolimus, alone or in combination. Rifampin and minocyline are a preferred combination of anti-microbial agents.

Leukotriene inhibitors/antagonists are anti-inflammatory agents and include, but are not limited to, leukotriene receptor antagonists such as acitazanolast, iralukast, montelukast, pranlukast, verlukast, zafirlukast, and zileuton.

Pharmaceutical Formulations:

The polymers and blends of the invention can be formulated as pharmaceutical compositions comprising one or more of those molecules, one or more drugs (as active ingredient), and a pharmaceutically acceptable carrier. Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical carriers are well known. In addition to the pharmacologically active agent, the compositions can contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds, as appropriate in oily injection suspensions may be administered. Suitable lipophilic solvents or vehicles include fatty oils, for example, sesame oil or synthetic fatty acid esters, for example, ethyl oleate or triglycerides. Aqueous injection suspensions can contain substances which increase the viscosity of the suspension, which include, for example, sodium carboxymethyl cellulose, sorbitol, and dextran. Optionally, the suspension can also contain stabilizers. Liposomes can also be used to encapsulate the agent for delivery into cells.

The pharmaceutical formulation for systemic administration according to the invention can be formulated for enteral, parenteral or topical administration. Indeed, all three types of formulations can be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

The polymers and blends of the invention can also be incorporated into pharmaceutical compositions which allow for the sustained delivery of those compounds to a mammal for a period of several days, to at least several weeks, to a month or more. Such formulations are described in U.S. Pat. Nos. 5,968,895 and 6,180,608 B1.

For topical administration, any common topical formation such as a solution, suspension, gel, ointment or salve and the like can be employed. The preparation of such topical formulations are well described in the art of pharmaceutical formulations as exemplified, for example, by Remington's Pharmaceutical Sciences. For topical application, the polymers and blends of the invention can also be administered as a powder or spray, particularly in aerosol form. The active ingredient can be administered in pharmaceutical compositions adapted for systemic administration. As is known, if a drug is to be administered systemically, it can be confected as a powder, pill, tablet or the like or as a syrup or elixir for oral administration. For intravenous, intraperitoneal or infra-lesional administration, the active ingredient can be prepared as a solution or suspension capable of being administered by injection. In certain cases, it may be useful to formulate the active ingredient in suppository form or as an extended release formulation for deposit under the skin or intramuscular injection. In a one embodiment, the polymers and blends of the invention may facilitate inhalation therapy. For inhalation therapy, the polymers or blends together, with the active ingredient, can be in a solution useful for administration by metered dose inhalers or in a form suitable for a dry powder inhaler.

Medical Devices:

The polymers and blends of the invention can be used to coat or form implantable prostheses used to reconstruct, reinforce, bridge, replace, repair, support, stabilize, position or strengthen any soft tissue defect. For example, soft tissue defects that can be treated in accordance with the instant invention include hernias, including but not limited to inguinal, femoral, umbilical, abdominal, incisional, intramuscular, diphragmatic, abdomino-throacic and thoracic hernias. The prostheses can also be used for structural reinforcement for muscle flaps, to provide vascular integrity, for ligament repair/replacement and for organ support/positioning/repositioning such as done with a bladder sling, a breast lift, or an organ bag/wrap. The prostheses can be used in reconstruction procedures involving soft tissue such as an orthopaedic graft support/stabilization, as supports for reconstructive surgical grafts and as supports for bone fractures. The prostheses are generally meshes, membranes or patches, and include woven or non-woven meshes and the like.

Additionally, the polymers and blends of the invention can be used to coat or to form wound closure adjuncts, such as staples, sutures, tacks, rings, screws, and the like.

The polymers and blends of the invention can also be used to coat meshes which are formed into or to form pouches, coverings, pockets and the like for implantable medical devices. Such implantable medical devices include, but are not limited to cardiac rhythm management devices such as a pacemaker, a defibrillator, a pulse generator as well as other implantable devices such as implantable access systems, neurostimulators, spinal cord stimulators, breast implants or any other implantable medical device. The coverings, pouches, pockets and the like hence can serve to secure those devices in position, provide pain relief, inhibit scarring or fibrosis, inhibit or prevent bacterial growth or infection, and deliver other drugs to the site of implantation.

The polymers and blends of the invention can also be used in conjunction with any implantable or insertable medical devices which has a temporary, or some time-limited therapeutic need as well as those with permanent function (such as joint replacements). For example, such polymers can be used to form fully resorbable vascular stents, which after a sufficient period of healing become completely resorbed while leaving a patent blood vessel. Fully resporbable stents may be used in conjunction with one or more drugs.

More detail and other examples of medical devices to which the present polymers and blends are useful include, but are not limited to, catheters (e.g., renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, femoral plugs, patches, pacemakers and pacemaker leads, heart valves, vascular valves, biopsy devices, patches for delivery of therapeutic agent to intact skin and broken skin (including wounds); tissue engineering scaffolds for cartilage, bone, skin and other in vivo tissue regeneration; sutures, suture anchors, anastomosis clips and rings, tissue staples and ligating clips at surgical sites; orthopedic fixation devices such as interference screws in the ankle, knee, and hand areas, tacks for ligament attachment and meniscal repair, rods and pins for fracture fixation, screws and plates for craniomaxillofacial repair; dental devices such as void fillers following tooth extraction and guided-tissue-regeneration membrane films following periodontal surgery; and various coated substrates that are implanted or inserted into the body.

Use of the polymers and blends with any of the medical devices described herein can include can be used with one or more drugs.

Accordingly, the present invention provides methods of treating a disorder or condition in a patient comprising implanting a medical device or a medical device assembly comprising a polymer or blend of the invention, e.g., as a coating, in conjunction with a covering or as the complete or partial device, by implanting the device in a patient, and particularly for disorders and conditions such as a cardiovascular disorder, a neurological disorder, a hernia or hernia-related disorder, an ophthalmic condition, or anatomical repair, reconstruction, replacement or augmentation.

In some embodiments, the method is used to implant a stent to treat atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

In other embodiments, the method is used to implant a surgical mesh to reconstruct, reinforce, bridge, replace, repair, support, stabilize, position or strengthen any soft tissue defect, including a hernia.

In yet other embodiments, the method is used to implant a medical device assembly such as a CRM in a covering or pouch, a neurostimulator in a pouch or covering, or a breast implant in a pouch or covering.

It will be appreciated by those skilled in the art that various omissions, additions and modifications may be made to the invention described above without departing from the scope of the invention, and all such modifications and changes are intended to fall within the scope of the invention, as defined by the appended claims. All references, patents, patent applications or other documents cited are herein incorporated by reference in their entirety for all purposes.

Example 1

General Methods

Molecular weight (Mol. Wt.) was determined by gel permeation chromatography (GPC) using 3 cross linked polystyrene columns run in DMF/0.1% TFA at 0.8 ml/m and measured against polyethylene glycol standards using an $R_1$ detector.

Tg values were determined by DSC using a heating ramp of 10° C./m. Reported values are computed from a $2^{nd}$ ramp cycle.

Proton nmr spectra were determined in $D_6MSO$ using tetramethylsilane as an internal calibration standard.

Example 2

Synthesis of Strictly Alternating $(Ab)_n$ Polymers

A. Synthesis of p(TE-Dg-TE 35% PEG400-Bis-Succinate:Adipate)

Step 1: Synthesis of TE-Dg-TE

Tyrosine ethyl ester free base (0.256 4 moles; 53.65 g) was reacted with diglycolic acid (0.1275 moles; 17.1 g) in presence of HOBT.H$_2$O and EDCI.HCl in N-methylpyrrolidinone (NMP) solvent. The reaction was carried out at 3-30° C. over a period of 16-18 h. Ethyl acetate was used during liquid-liquid extraction purification. Yield: 90%. Melting point: 128-129° C. Mass: 517.21(M+1).

NMR: 9.2-9.25 ppm (2H, singlet), 8.25-8.32 ppm (2H, doublet), 6.95-7.15 ppm (4H, doublet), 6.6-6.7 ppm (4H, doublet), 4.4-4.5 ppm (2H, quartet), 4.0-4.01 ppm (4H, quartet), 3.85-3.98 ppm (4H, quartet), 2.82-2.89 ppm (4H, multiplet), 1.08-1.16 ppm (6H, triplet).

Step 2: Synthesis of p(TE-Dg-TE 35% Peg400-Bis-Succinate:Adipate)

TE-Dg-TE (0.1 moles; 51.66 g) was reacted with PEG400-bis-succinic acid (0.035 moles; 22.27 g) and adipic acid (0.065 moles; 9.5 g) in presence of DPTS and diisopropylcarbodimide (DIPC) in methylene chloride solvent. The reaction was carried out at 32-38° C. over a period of 18-20 h. Isopropyl alcohol was used in precipitation of the polymer. Yield: 88%. GPC: >100 kDa. Tg: 19-22° C.

NMR: 8.37-8.38 ppm (d, 1H), 7.24-7.26 ppm (m, 4H), 6.99-7.02 ppm (m, 4H), 4.48-4.55 ppm (q, 1H), 4.15-4.2 ppm (t, 4H), 4.0-4.04 ppm (q, 2H), 3.88-3.96 ppm (m, 4H), 3.59-3.65 ppm (t, 4H), 3.47-3.54 ppm (m, 32H), 2.95-3.1 ppm (m, 1H), 2.81-2.86 ppm (t, 4H), 2.67-2.70 ppm (t, 4H), 2.62-2.68 ppm (m, 4H), 1.72-1.82 ppm (m, 4H), 1.1-1.15 ppm (t, 3H).

B. Synthesis of p(TE Diglycolate) Alternating

This synthesis generally followed the same steps as in section A of this example, except that step 2 used the same diacid as in the first step, namely diglycolic acid. Yield: 75%. Mol. Wt.: 47 kDa. Polydispersity index (PDI): 1.25. Tg: 56.1° C.

NMR: 8.45 ppm (2H, NH, d), 8.3 ppm and 8.2 ppm (<0.1H, NH, doublets), 7.3 ppm 7.1 ppm (8H, aromatic, a.sup.2b.sup.2), 4.45 ppm (2H, methinyl, m), 4.1 ppm (4H, diglycolate, q), 3.9 ppm (4H, O—CH$_2$, q), 3.1 ppm (4H, benzylic, m), 1.1 ppm (6H, terminal methyl, q/m).

C. Synthesis of p(TE Glutarate) Alternating

This synthesis generally followed the same steps as in section A of this example, except that in except that in step 1, the diacid was glutaric acid and in step 2, the same diacid was also used, namely glutaric acid. Yield: 61%. Mol. Wt.: 60 kDa, PDI: 1.24, Tg: 70° C.

NMR: 8.45 ppm 8.35 ppm (2H, NH doublets: 1: 14), 7.3 ppm 7.1 ppm (total 8H, aromatic, a.sup.2b.sup.2), 4.45 ppm (2H, methinyl, m), 4.1 ppm (4H, O—CH$_2$, m), 2.8 ppm (4H, terminal glutaryl, m), 2.7 ppm (4H, benzylic, m), 1.6 ppm (2H, central glutaryl, m), 1.1 ppm (6H, terminal methyl, t).

D. Synthesis of Polymers in Table 1

The synthesis for these polymers was generally done as described in section A of this example using the indicated aminophenol, timers and diacids. Table 1 provides the molecular weights (determined by GPC) and the Tg of many of these polymers.

Example 3

Synthesis of Random AP—X Polmers

A. General Synthesis Route

The random polymers were generally synthesized as described in U.S. Pat. Nos. 5,216,115 and 5,597,507 using a carbodimide-mediated coupling reaction. Briefly, equimolar amounts of the aminophenol and the diacid were condensed in methylene chloride using DIPC as the coupling agent in the presence of 4-dimethylaminopyridium para-toluene sulfonic acid (DPTS). For polymers which contain a free acid moiety, a similar synthesis was conducted by first synthesizing the corresponding benzyl ester containing polymer (i.e., the aminophenol had a benzyl ester) followed by hydrogenation as described in U.S. Pat. No. 6,120,491 to yield the free acid-containing polymer. The polymers were usually isolated by repeated precipitation from isopropanol.

B. Synthesis of p(TE Diglycolate) Random

The synthesis was as generally described in Section A of this example, using tyrosine ethyl ester as the aminophenol and diglycolic acid as the diacid. Yield: 60%. Mol. Wt. 27 kDa. PDI: 1.50. Tg: 54.5° C.

NMR: 8.45 ppm 8.35 ppm (2H, NH doublets: 1:1.6), 7.3 ppm 7.1 ppm (total 8H, aromatic, a.sup.2b.sup.2), 4.45 ppm (2H, methinyl m), 4.1 ppm (4H, O—CH$_2$, m), 2.9 ppm (4H, terminal glutaryl, m), 2.7 ppm 2.4 ppm (4H, benzylic, m), 1.8 ppm (2H, central glutaryl, m), 1.1 ppm (6H, terminal methyl, t).

C. Synthesis of p(TE Glutarate) Random

The synthesis was as generally described in Section A of this example, using tyrosine ethyl ester as the aminophenol and glutaric acid as the diacid. Mol. Wt.: 44 kDa; PDI: 1.19; Tg: 68° C.

D. Synthesis of p(TE Succinate) Random

The synthesis was as generally described in Section A of this example, using tyrosine ethyl ester as the aminophenol and succinic acid as the diacid.

Example 4

Polymer Degradation and Mass Loss Studies

For these studies, the indicated polymer and drug(s), if present, were dissolved in an organic solvent and spray coated onto a surgical polypropylene mesh. Typically, a 1% solution of polymer or of a ratio of 1:1:8 rifampin:minocycline:polymer in 9:1 tetrahydrofuran/methanol is spray-coated onto a surgical mesh by repeatedly passing the spray nozzle over each side of the mesh until each side is coated with the desired amount of antimicrobial-embedded polymer. Meshes are dried for at least 72 hours in a vacuum oven before use and cut to size for degradation studies.

Molecular weight (MW) profile: For monitoring MW decrease as a function of time, meshes are incubated with 0.01 M PBS or 0.01M PBS with Tween20 (50 to 100 mL) at 37° C. with shaking. At each time point, polymer samples are dissolved in solvent, filtered and transferred to analysis vials for analysis by gel permeation chromatography (GPC).

Mass loss profile: For mass loss analysis, meshes are incubated with 0.01 M PBS or 0.01M PBS with Tween 20 (50 to 100 mL) at 37° C. with shaking. The buffer in the vials is changed at periodic intervals and analyzed for soluble degrading components. At each time point, 1-2 mL buffer from three small vials are filtered and transferred to analysis vials for analysis by reversed phase HPLC. Alternately, the devices can be washed, dried and weighed (final weight) and the mass loss determined by subtracting the final weight from the original weight.

Figure 2:
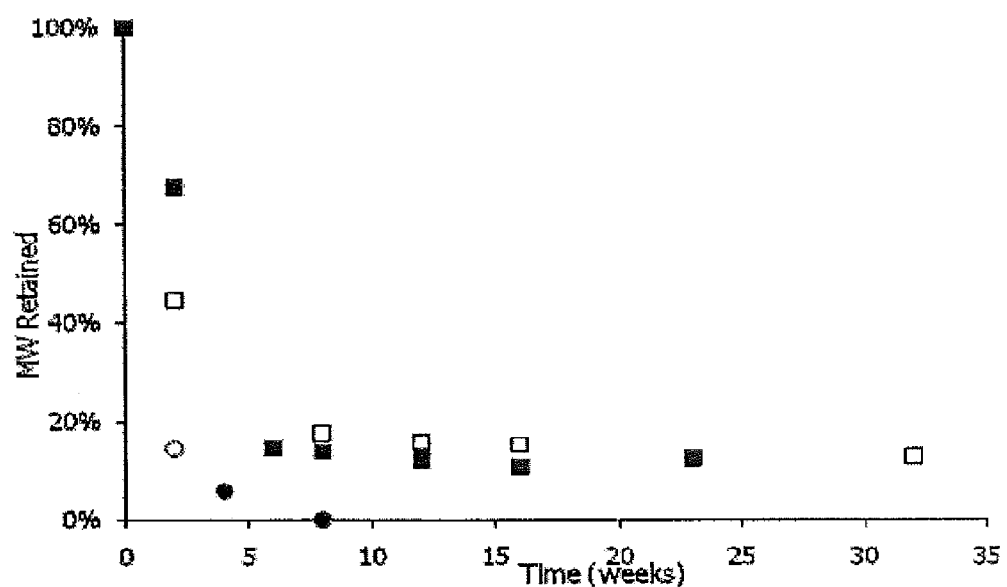
FIG. 2 graphically illustrates molecular weight retained under physiological degradation conditions for random and alternating polymers on polymer-coated meshes: (□) TE glutarate alternating; (■) TE glutarate random; (○) TE diglycolate alternating; (●) TE diglycolate random.
Figure 3:
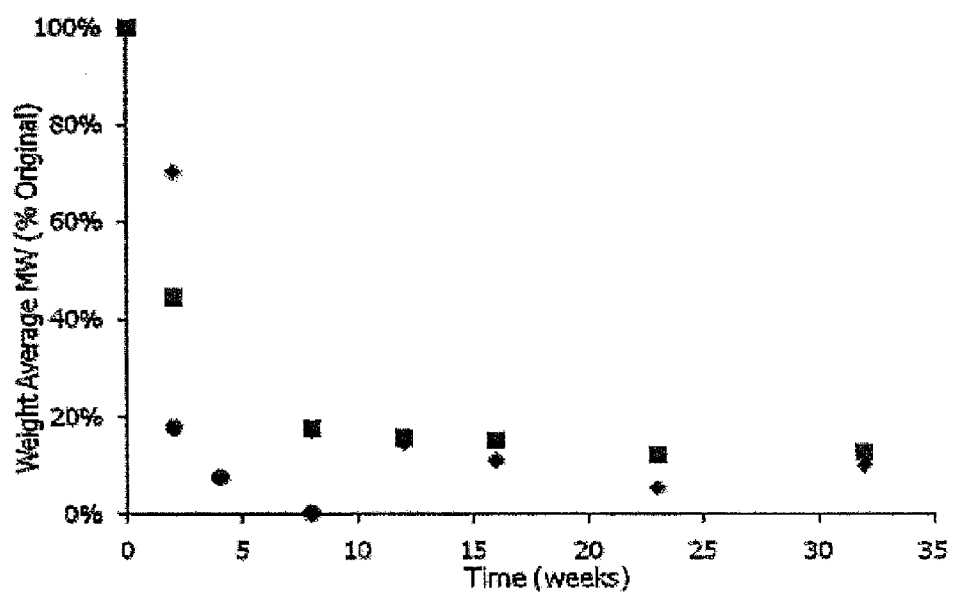
FIG. 3 graphically illustrates molecular weight retained under physiological degradation conditions for three different random polymers on polymer-coated meshes: (♦) TE succinate; (■) TE glutarate; (●) TE diglycolate.

The results for mass retained under physiological degradation conditions for random and alternating polymers on polymer-coated meshes is shown in FIG. 1. The results for molecular weight retained under physiological degradation conditions for random and alternating polymers is shown in FIG. 2 and, for three different random polymers is shown in FIG. 3.

Example 5

Drug Release Studies

Polymer films are made by dissolving sufficient polymer in 9:1 tetrahydrofuran (THF) and methanol (MeOH) to yield a 10% (w/v) polymer solution. After the polymers are dissolved, rifampin and minocycline are added to reach 3% of each drug in solution and mixed well. Polypropylene or delrin molds in the shape of a breast implant are fixed onto a holder and dipped slowly into and slowly out of the solution using a dipping machine from DipTech Systems, Inc with 10-60 min intervals between each successive dip. The dipped molds are dried at room temperature in a blow oven for 5 h followed by drying in a 50° C. oven for 16 h. After drying, the molded polymer produces a breast implant covering that is easily peeled from the mold. This covering is further dried off mold at 50° C. for 72 h. Small discs or pieces are cut from these coverings and used for drug release studies.

Alternatively, the solution can be poured onto a TEFLON coated glass surface and spread to 0.25 mm with a spreading knife. The film is covered by an aluminum foil wrapped glass dish and dried at room temperature overnight. The film is peeled off and put in an amber bag and dried in a vacuum oven at 50° C. for 3 days. The dried film is cut into small pieces of about 10 mg.

When coated meshes are used, the meshes are spray coated as described in Example 4, and after drying, are cut into pieces for drug release studies.

The discs, pieces or meshes are placed into a 20 mL vial containing 10 mL of PBS. Aliquots of buffer are removed periodically for analysis and replaced with fresh buffer. Samples are analyzed by HPLC to determine the cumulative amount of released rifampin and/or minocycline.

Figure 4:
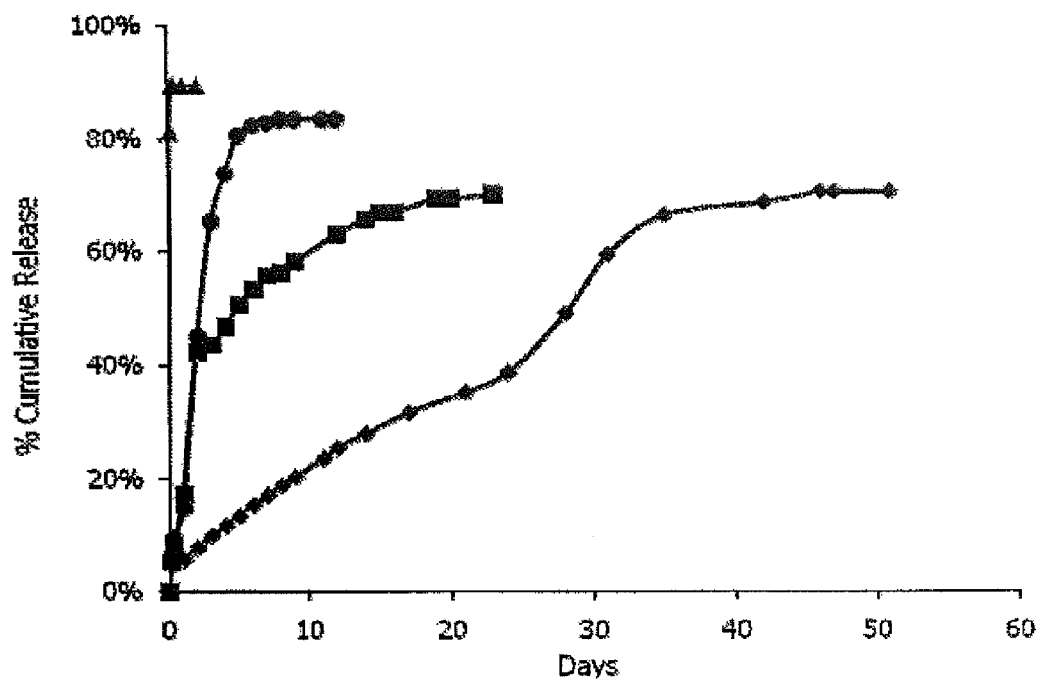
FIG. 4 graphically illustrates the cumulative percentage release of rifampin under physiological conditions from four random polymers on polymer-coated meshes: (♦) TE succinate; (■) TE glutarate; (●) TE diglycolate; (▲) TE:15T glutarate.

The results in FIG. 4 show the cumulative percentage release of rifampin under physiological conditions for four random polymers on polymer-coated meshes: TE succinate; TE glutarate; TE diglycolate; and TE:15T glutarate.

Example 6

Comparative Molecular Weight and Mass Losses

Figure 5:
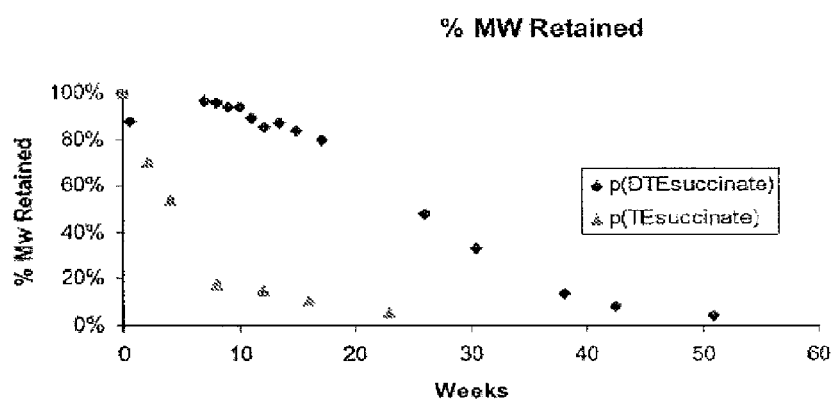
FIG. 5 graphically compares molecular weight loss under physiological conditions for a tyrosine-derived diphenol polymer, p(desaminotyrosyl tyrosine ethyl ester succinate) (♦) relative to p(TE succinate) (▲). The polymer p(desaminotyrosyl tyrosine ethyl ester succinate) is abbreviated as p(DTE succinate).

Molecular weight is determined as described in Example 4 for p(DTE succinate) and a polymer of the invention, p(TE succinate) spray coated on to polypropylene meshes. The molecular weight loss, expressed as molecular weight retained, is shown in FIG. 5.

Figure 6:
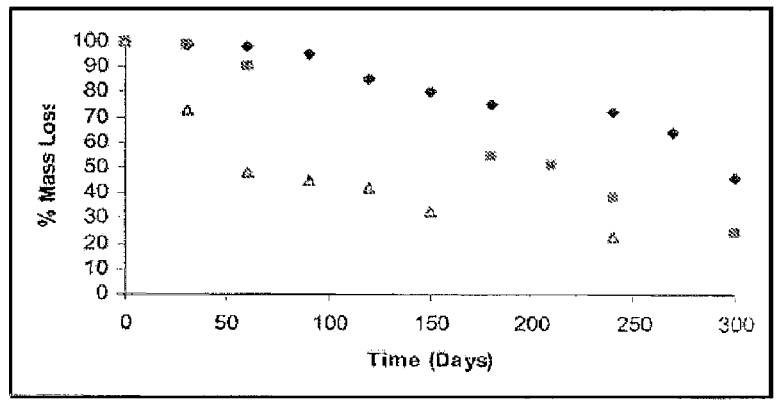
FIG. 6 graphically compares the mass loss of p(10% desaminotyrosyl tyrosine 90% desaminotyrosyl tyrosine ethyl ester succinate) (♦), p(15% desaminotyrosyl tyrosine 85% desaminotyrosyltyrosine ethyl ester succinate) (■), and TEsuccinate (▲).
Figure 7:
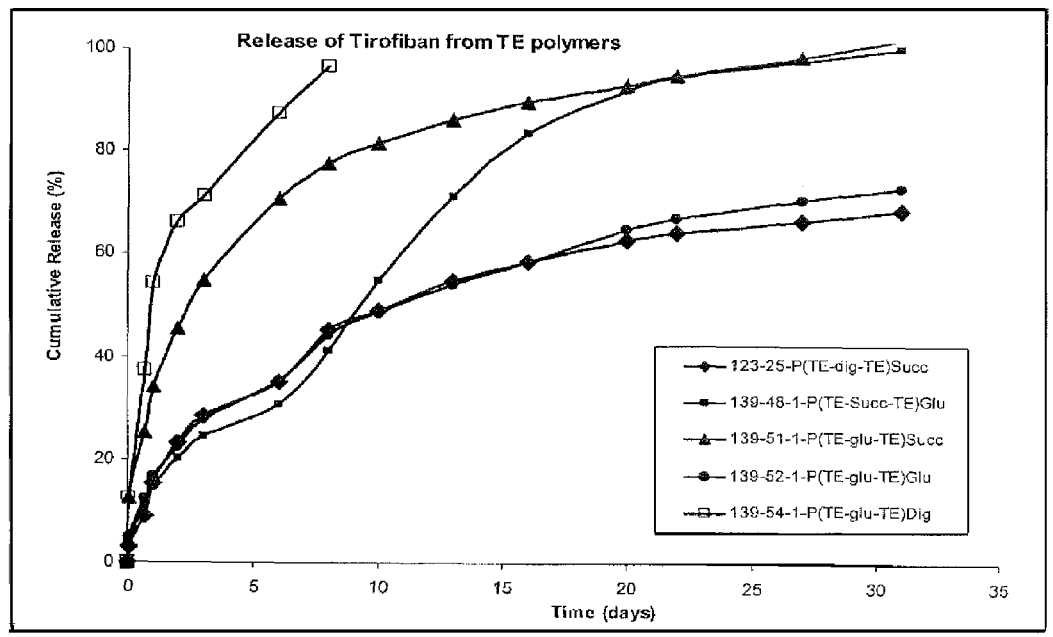
FIG. 7 graphically illustrates the release of tirofiban from various polymers of the present invention.

A comparative example of mass loss is provided in FIG. 6 in which the mass loss under physiological conditions on spray-coated polypropylene meshes is shown for two tyrosine-derived diphenol polyarylates—p(10% desaminotyrosyl tyrosine 90% desaminotyrosyl tyrosine ethyl ester succinate) and p(15% desaminotyrosyl tyrosine 85% desaminotyrosyltyrosine ethyl ester succinate)—relative to a polymer of the invention-p(TE succinate).

The invention claimed is:

1. A synthetic polymer comprising monomer units represented by the formula:

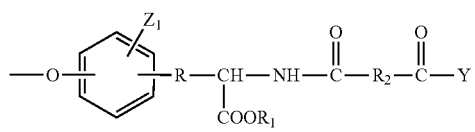

wherein R is —$(CR_3R_4)_a$— or —$CR_3$=$CR_4$—;

$R_1$ is hydrogen; saturated or unsaturated alkyl, aryl, alkylaryl or alkyl ether having from 1 to 20 carbon atoms; or —$(R_5)_qO((CR_3R_4)_rO)_s$—$R_6$;

each $R_2$ is independently a divalent, linear or branched, substituted or unsubstituted alkylene, alkenylene, alkynylene, arylene, alkylarylene, divalent alkyl ether or aryl ether moiety having from 1 to 30 carbon atoms; —$(R_5)_qO((CR_3R_4)_rO)_s(R_5)_q$—; or —$(R_5)_qCO_2((CR_3R_4)_rO)_sCO(R_5)_q$—;

$R_3$ and $R_4$ are each independently, hydrogen or linear or branched, substituted or unsubstituted alkyl having from 1 to 10 carbon atoms, $R_5$ is independently linear or branched lower alkylene or lower alkenylene;

$R_6$ is independently linear or branched, substituted or unsubstituted, saturated or unsaturated lower alkyl;

the aromatic ring has from zero to four $Z_1$ substituents, each of which is independently selected from the group consisting of halide, lower alkyl, alkoxy, nitro, alkyl ether, a protected hydroxyl group, a protected amino group and a protected carboxylic acid group;

Y is $(bc)_n$, b is

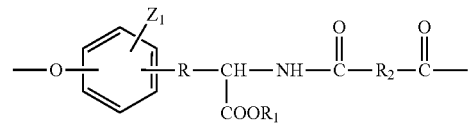

c is

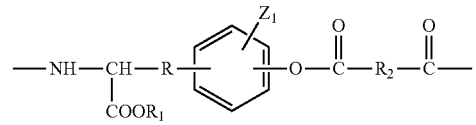

n is a number of repeat units;
a is 0 to 10;
each q is independently 1 to 4;
each r is independently 1 to 4; and
each s is independently 1 to 5000.

2. A synthetic polymer as recited in claim 1, wherein the number of repeat units is an average weight of the synthetic polymer divided by a molecular weight of bc.

3. A pharmaceutical composition comprising the synthetic polymer of claim 1 and one or more drugs.

4. A pharmaceutical composition as recited in claim 3, wherein the one or more drugs are selected from a group consisting of antimicrobial agents, antibacterial agents, aneshetics, anti-inflammatory agents, anti-scarring agents, anti-fibrotic agents, leukotriene inhibitors and chemotherapeutic agents.

5. A pharmaceutical composition as recited in claim 3, wherein the one or more drugs is an antimicrobial agent selected from a group consisting of rifampin, minocycline, gentamicin, vancomycin, triclosan, and combinations thereof.

6. A synthetic polymer as recited in claim 3, wherein the one or more drugs are selected from a group consisting of rifampin, minocycline, anesthetics and anti-inflammatory agents.

7. A synthetic polymer as recited in claim 1, wherein $R_1$ is independently selected from a group consisting of hydrogen, methyl, ethyl, propyl, butyl and benzyl.

8. A synthetic polymer as recited in claim 7, wherein R is methylene or ethylene.

9. A synthetic polymer as recited in claim 1, wherein R is methylene or ethylene.

10. A synthetic polymer as recited in claim 1, wherein $R_2$ is independently selected from a group consisting of methyl, ethyl, n-propyl, —$CH_2OCH_2$—, —$(CH_2)_qCO_2$—$(CH_2CH_2$—$O)_s$—$C(O)$—$(CH_2)_q$—, and —$(CH_2)_qO(CH_2CH_2O)_s(CH_2)_q$—.

11. A medical device comprising the synthetic polymer of claim 1.

12. A medical device as recited in claim 11, wherein the medical device is a stent, a coated stent, a surgical mesh, a film coated device, a device covering or a catheter.

13. A medical device as recited in claim 11, further comprising one or more drugs.

14. A medical device as recited in claim 13, wherein the one or more drugs are selected from a group consisting of antimicrobial agents, antibacterial agents, aneshetics, anti-inflammatory agents, anti-scarring agents, anti-fibrotic agents, leukotriene inhibitors and chemotherapeutic agents.

15. A medical device as recited in claim 13, wherein the one or more drugs is an antimicrobial agent selected from a group consisting of rifampin, minocycline, gentamicin, vancomycin, triclosan, and combinations thereof.

16. A medical device as recited in claim 13, wherein the one or more drugs are selected from a group consisting of rifampin, minocycline, anesthetics and anti-inflammatory agents.

17. A medical device comprising the medical device and a coating on or adhered to a surface of the medical device, the coating comprising one or more layers of the synthetic polymer of claim 1.

18. A medical device as recited in claim 17, wherein one or more layers of said coating further comprises one or more drugs.

19. A blend of polymers comprising the synthetic polymer of claim 1 and one or more second polymers.

20. A blend of polymers as recited in claim 19, wherein the one or more second polymers is selected from a group consisting of polylactic acid, polyglycolic acid and copolymers and mixtures thereof, poly(L-lactide) (PLLA), poly(D,L-lactide) (PLA), polyglycolic acid [polyglycolide (PGA)], poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), poly(D,L-lactide-co-caprolactone) (PLA/PCL) and poly(glycolide-co-caprolactone) (PGA/PCL); poly(oxa)esters, polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly(phosphazene), poly(phosphate ester), poly(amino acid), polydepsipeptides, maleic anhydride copolymers, polyiminocarbonates, poly[(97.5% dimethyl-trimethylene carbonate)-co-(2.5% trimethylene carbonate)], poly(orthoesters), tyrosine-derived polyarylates, tyrosine-derived polycarbonates, tyrosine-derived polyiminocarbonates, tyrosine-derived polyphosphonates, polyethylene oxide, polyethylene glycol, polyalkylene oxides, hydroxypropylmethylcellulose, polysaccharides such as hyaluronic acid, chitosan, regenerated cellulose, proteins, gelatin, collagen, mixtures and copolymers thereof, and PEG derivatives or blends of any of the foregoing.

21. A synthetic polymer as recited in claim 1, selected from a group consisting of p(TE succinate), p(TE succinate alternating), p(TE glutarate), p(TE glutarate) alternating, p(TE diglycolate), p(TE diglycolate) alternating, p(TE:15T glutarate) and p(TE:15TBz glutarate).

\* \* \* \* \*